(12) United States Patent
Amini et al.

(10) Patent No.: US 11,672,510 B2
(45) Date of Patent: Jun. 13, 2023

(54) ESTIMATION OF VIBRATION AMPLITUDE AND ELASTIC PROPERTIES OF EXTRA-CAPILLARY TISSUE WITH ULTRASOUND DRIVEN VIBRATION OF INTRA-CAPILLARY GAS BUBBLES

(71) Applicant: SURF Technology AS, Trondheim (NO)

(72) Inventors: Seyednaseh Amini, Trondheim (NO); Bjorn Angelsen, Trondheim (NO); Stian Solberg, Florvåg (NO); Yamen Zaza, Trondheim (NO)

(73) Assignee: SURF TECHNOLOGY AS, Trondheim (NO)

( * ) Notice: Subject to any disclaimer, the term of this patent is extended or adjusted under 35 U.S.C. 154(b) by 0 days.

(21) Appl. No.: 17/953,087

(22) Filed: Sep. 26, 2022

(65) Prior Publication Data

US 2023/0112529 A1    Apr. 13, 2023

Related U.S. Application Data

(60) Provisional application No. 63/248,180, filed on Sep. 24, 2021.

(51) Int. Cl.
*A61B 8/00* (2006.01)
*A61B 8/08* (2006.01)
*G01S 15/89* (2006.01)

(52) U.S. Cl.
CPC .......... *A61B 8/485* (2013.01); *G01S 15/8952* (2013.01)

(58) Field of Classification Search
CPC ............................... A61B 8/485; B06B 1/0614
See application file for complete search history.

(56) References Cited

U.S. PATENT DOCUMENTS 7,727,156 B2    7/2010  Angelsen
8,550,998 B2   10/2013  Angelsen
(Continued)

FOREIGN PATENT DOCUMENTS

CN    112933435    6/2021

OTHER PUBLICATIONS

Search Report with Written Opinion dated Jan. 27, 2023 issued in International Patent Application No. PCT/IB2022/00552.

*Primary Examiner* — Rajeev P Siripurapu
(74) *Attorney, Agent, or Firm* — Cozen O'Connor

(57) ABSTRACT

Estimation of vibration amplitude of intra-capillary microbubbles driven to vibrate with an incident ultrasound wave with amplitude and frequency to adjust the drive amplitude of the incident wave to obtain specified vibration amplitude of extra-capillary tissue. Estimation uses transmission of M groups of pulse complexes having low frequency pulse (LF) at bubble drive frequency, and high frequency (HF) pulse with angular frequency $\omega_H > \sim 5\omega_L$, and pulse duration shorter than $\pi/4\omega_L$ along HF beam. The phase between HF and LF pulses is $\omega_L t_m$ for each group, where $t_m$ varies between the groups. Within each group, LF pulse varies between pulse complexes in amplitude and/or, where the LF pulse can be zero for a pulse complex, and LF pulse is different from zero for pulse complex within each group. HF receive signals are processed to obtain a parameter relating to bubble vibration amplitude when the HF pulse hits bubble.

36 Claims, 12 Drawing Sheets

(56) References Cited

U.S. PATENT DOCUMENTS

| | | |
|---|---|---|
| 9,291,493 B2 | 3/2016 | Angelsen |
| 9,743,909 B1 | 8/2017 | Sapozhnikov et al. |
| 9,939,413 B2 | 4/2018 | Angelsen |
| 10,578,725 B2 | 3/2020 | Angelsen |
| 10,879,867 B2 | 12/2020 | Angelsen et al. |
| 2007/0035204 A1 | 2/2007 | Angelsen et al. |
| 2010/0036244 A1 | 2/2010 | Angelsen et al. |
| 2019/0235076 A1 | 8/2019 | Angelsen et al. |
| 2020/0405268 A1 | 12/2020 | Angelsen |

$l_c = 10$ μm $l_c = 15$ μm $l_c = 20$ μm $l_c = 25$ μm

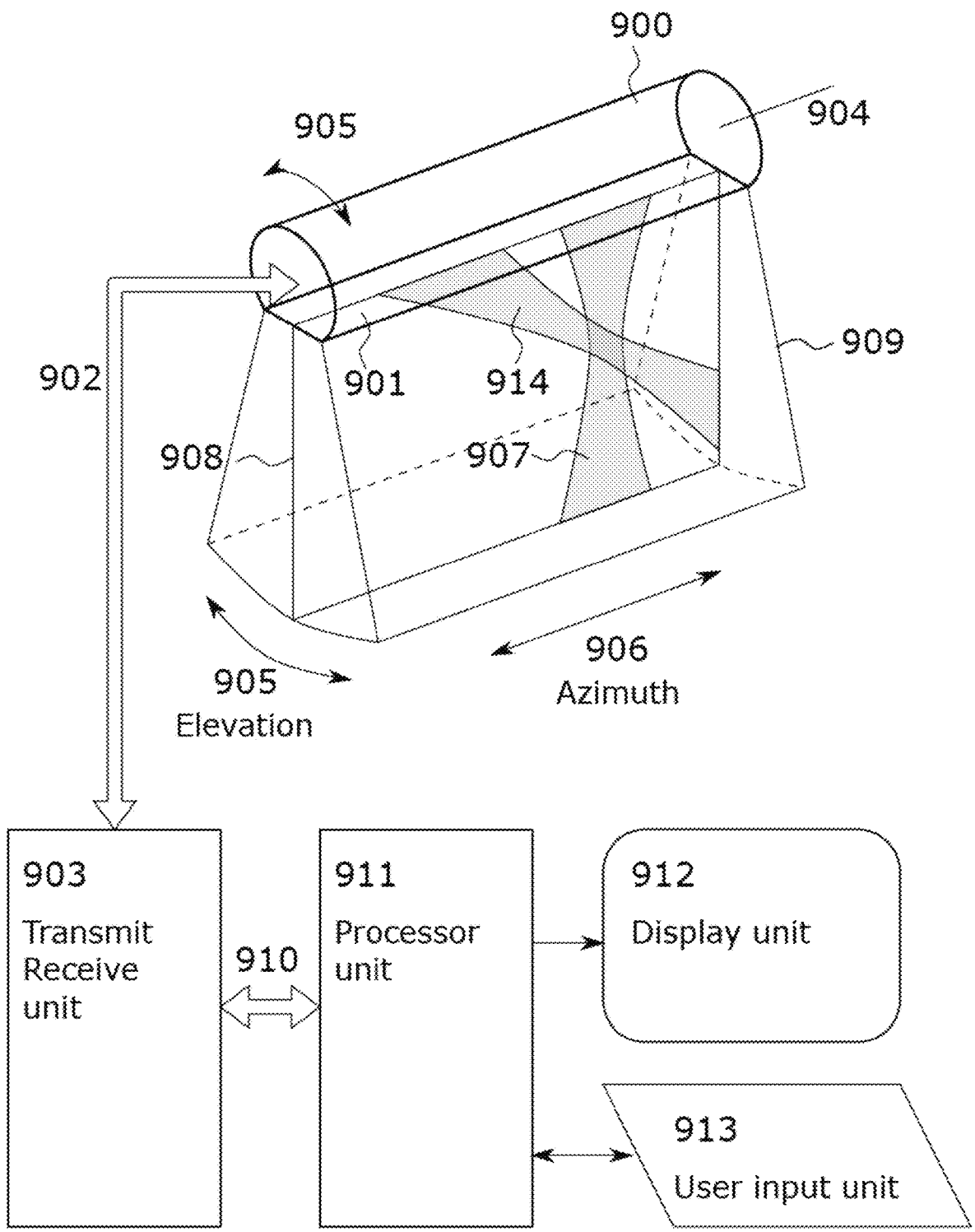
FIG. 9 INSTRUMENT BLOCK DIAGRAM

ESTIMATION OF VIBRATION AMPLITUDE AND ELASTIC PROPERTIES OF EXTRA-CAPILLARY TISSUE WITH ULTRASOUND DRIVEN VIBRATION OF INTRA-CAPILLARY GAS BUBBLES

RELATED APPLICATION

This application claims priority from U.S. provisional patent application No. 63/248,180 filed on Sep. 24, 2021, the entire content of which is incorporated by reference.

FIELD OF THE INVENTION

The invention addresses methods and instrumentation for using ultrasound vibrations of intra-capillary micro-bubbles to increase fluid to gas phase transition of fluor-carbon (FC) droplets in humans.

DISCUSSION OF RELATED ART

Liquid to gas phase transition of perfluor-carbon nano- and micron-droplets is an emerging field for improving ultrasound diagnosis and assisted therapy of diseases such as cancer, inflammation, atherosclerosis, and myocardial infarction.

Ultrasound stimulated phase transition of ~3 μm diameter Per-Fluor-Carbon (PFC) droplets produces micro-bubbles of ~15 μm diameter in larger arteries. In capillaries with typical diameters ~6-10 μm, such gas bubbles fills the capillary for ~30-100 μm length with a slow absorption decay into blood over some minutes. Ultrasound vibration of the intra-capillary bubbles produces vibration of the extra-capillary tissue ~1 μm and has shown to increase efficacy of cancer chemotherapy in pre-clinical studies. There are also indications that such intra-capillary bubble vibrations can increase the immune response to a particular cancer in association with other therapies, and reduce myocardial hypoxia after coronary reopening after a cardiac ischemia attack.

The therapeutic effect depends on adequate amplitude of the capillary wall vibrations. Bubbles obtained by evaporation of PFC droplets of ~3 μm diameter produce resonance frequencies around ~500 kHz, and to obtain desirable vibration amplitude of the capillary wall one wants to vibrate the bubbles close to their resonance frequency. The vibration amplitude depends on the amplitude and frequency of the incident ultrasound drive wave, the capillary dimension, and particularly also the shear stiffness of the extra capillary tissue. Especially can both the capillary diameter and the shear stiffness and absorption of the extra-capillary tissue vary by a large amount between different cases. It is therefore desirable to have an online assessment of the vibration amplitude of bubbles that fills the capillary. The invention presents new methods and instrumentation that produces estimates of both the bubble vibration amplitude and its resonance frequency, and also extracts elastic information of tissue surrounding the bubbles.

SUMMARY OF THE INVENTION

An overview of the invention is presented, where the overview is a short form and by no means represents limitations of the invention, which in its broadest aspect is defined by the claims appended hereto.

The invention presents methods and instrumentation for estimation of vibration amplitude of intra-capillary micro-bubbles that fills the capillary for a length and are driven to vibrate with an incident ultrasound wave of given amplitude and frequency. The estimated amplitude is for example used to adjust the drive amplitude of the incident wave to obtain a desired vibration amplitude of the extra-capillary tissue.

The estimation method comprises transmitting towards said micro-bubble a set of limited duration pulse complexes comprising a low frequency (LF) pulse along a LF transmit beam (T-beam) with angular frequency at close to the typical vibration drive frequency, and a high frequency (HF) pulse with angular frequency $\omega_H > \sim 5\, \omega_L$, and pulse duration shorter than $\pi/4\, \omega_L$ along a HF transmit beam (T-beam), where said LF T-beam overlaps the HF T-beam with essentially the same beam direction, and said set of pulse complexes are transmitted in a set of M groups, each group comprising at least two pulse complexes where the phase relation between the HF and LF pulses is $\omega_L t_m$ for each group where $t_m$ varies between the groups, and within each group the LF pulse varies between pulse complexes in one or both of the amplitude and polarity, where the LF pulse can be zero for a pulse complex, and the LF pulse is different from zero for at least one pulse complex, and obtaining for each pulse complex within each group, HF receive signals from the scattered HF waves from said micro-bubble with a HF receive beam with beam axis either along the HF transmit beam axis or crossing the HF beam axis, and processing for each group said HF receive signals from the transmitted pulse complexes with HF pulse phase relation $\omega_L t_m$ the LF pulse, to obtain a parameter relating to the bubble vibration amplitude when the HF pulse hits the bubble for said each pulse complex, and selecting said parameter from the group that gives the maximal vibration amplitude as an indication of the vibration amplitude of said micro-bubble.

The invention further includes instrumentation for carrying through the methods of estimation in a practical situation.

BRIEF DESCRIPTION OF THE DRAWINGS

FIG. 9 Illustrates an overview block diagram of a system for carrying through the methods according to the invention.

DETAILED DESCRIPTION OF EMBODIMENTS

This section gives a more detailed description of example embodiments of the invention, where the examples by no means represents limitations of the invention, which in its broadest aspect is defined by the claims appended hereto.

A. Fundamental Bubble Vibration

The invention presents methods and instrumentation for extracting information about ultrasound driven vibrations of micro-bubbles in tissue, and also to use this information for estimation of tissue properties, such as elastic properties, and properties relating to elastic properties.

Figure 1A:
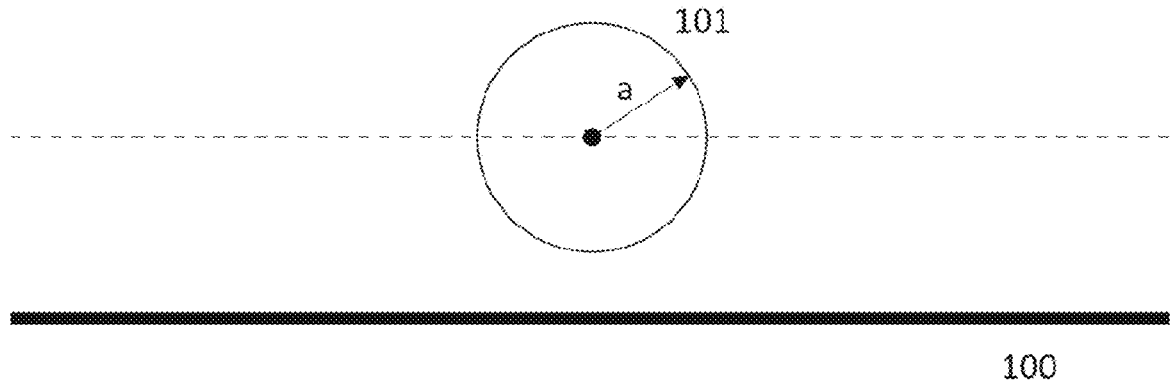
FIG. 1a Illustrates a spherical micro-bubble with radius a in a larger vessel.

The invention is relevant for micro-bubbles with diameter less than the capillaries, and also bubbles that in large arteries have a spherical shape with radius a ~5-30 μm that gives a bubble volume $V_b=4\pi a^3/3$, while in capillaries with radii $a_V$~3-5 μm the larger bubbles fill at least part of the capillary. Examples of the larger bubbles are shown in FIG. 1, where 101 shows a spherical bubble in a larger artery 100, while 111 shows the a bubble filling a smaller capillary 110 with radius $a_V$ for a cylindrical length $2l_c$ with two semi-spherical endings 112 of radius $a_V$.

There is spatially distributed elasticity and mass density of the tissue, the blood, and the gas, that implies wave propagation with reflection at boundaries. The tissue and the blood have both a high volume compression stiffness $\lambda_t=1/\kappa_t$ ($\kappa_t$—volume compressibility) that upholds pressure waves with propagation velocity $c_p$≈1500 m/s for both tissue and blood. The tissue has in addition a low shear/deformation stiffness $\mu_t$ that produces tissue shear/deformation waves with no volume compression and low propagation velocity $c_s$~2-20 m/s. The blood and the gas have negligible shear stiffness, and hence no shear waves. The bubble gas has a low volume compression stiffness, but the mass density is also so low that the gas pressure can be approximated as constant across the bubble volume. The bubble gas pressure depends on the bubble volume and its variation as $$P_g = P_0\left(\frac{V_b}{V_b + \delta V}\right)^\gamma \approx P_0 - \gamma P_0 \frac{\delta V}{V_b} \quad (1)$$

$$\gamma = \frac{C_p}{C_V} \approx 1$$

$$\gamma = C_p/C_V \approx 1$$

where $P_0$~100 kPa is the environmental pressure, $V_b$ is the equilibrium bubble volume, $\delta V$ is the change in bubble volume, $C_p$ and $C_V$ are the heat capacities at constant pressure and volume. Typical gases have large molecules that makes $C_p \approx C_V$ and $\gamma \approx 1$. The volume-pressure relation is inherently nonlinear for larger changes in the volume, but we shall in our work use the approximate linear variation with $\delta V/V_b$, to study fundamental aspects of the bubble vibration.

The low tissue shear stiffness allows large deformations of the cylindrical bubble surface 111, with large amplitude, short-range shear deformation of the surrounding tissue with comparatively low volume compression. The large vibration amplitude of the close surrounding tissue produces an outward acoustic radiation force (ARF) that has interesting applications for drug transport both across the capillary wall, through the interstitial space between the tissue cells, and across membranes of the cells and other tissue structures. In this context it is important to obtain adequate bubble/tissue vibration amplitude (~1 μm) and one target of this invention is to use ultrasound scattering from vibrating bubbles to measure the bubble vibration amplitude produced by an incident ultrasound wave. The invention further uses the measured bubble vibration amplitude to set the amplitude of the incident vibration wave to achieve desired bubble vibration amplitude in the surrounding tissue to achieve the desired therapeutic effect.

A bubble in a large vessel, as 101 in 100, has a practically spherical shape with a spherical vibration pattern. A drive pressure $P_d$ that is the difference between the gas pressure $P_g$ and the pressure $P_\infty$ at a point so distant from the bubble that one can neglect the tissue shear vibration, produces a complex volume vibration amplitude $\Box V_c$ of the bubble as [1]

$$\frac{\delta V_c}{V_b} = H_d(\omega)P_d \quad H_d(\omega) \approx \frac{-K_d}{\omega^2 - \omega_d^2 - i2\zeta\omega_d\omega} \quad (2)$$

$$K_d = \frac{3}{\rho a^2} \quad \omega_d^2 = \frac{4E_{st}}{\rho a^2} \quad 2\zeta\omega_d = \frac{4\eta_b}{\rho a^2}$$

where $\rho_b$ and $\eta_b$ are the mass density and coefficient of viscosity of the surrounding blood, and $E_{st}$ is the Youngs module of the blood/gas surface layer. We refer to $H_d$ as the direct drive transfer function, and $\omega_d$ as the direct drive angular resonance frequency produced by the interaction between the co-oscillating mass of the surrounding blood and the elasticity of the blood/gas surface layer. Viscous friction in the blood and the surface layer is given by $\eta_b$.

An incident acoustic wave with pressure amplitude $P_i$ and angular frequency w produces a variation in the bubble volume and the gas pressure that produces drive pressure amplitude $P_d$ as $$P_d = -\gamma P_0 \delta V_c / V_b - P_i = -\gamma P_0 H_d(\omega) P_d - P_i \quad (3)$$

$$P_d = \frac{-P_i}{1 + \gamma H_d(\omega) P_0}$$

which gives the complete transfer function $H_V(\omega)$ from the incident pressure amplitude $P_i$ to the complex relative volume amplitude as $$\frac{\delta V_c}{V_b} = -H_V(\omega) P_i \quad (4)$$

$$H_V(\omega) = \frac{H_d(\omega)}{1 + \gamma H_d(\omega) P_0}$$

With the $2^{nd}$ order form of the $H_d(\omega)$ in Eq.(2), we get the following form of $H_V(\omega)$ $$H_V(\omega) = \frac{-K_d}{\omega^2 - \omega_0^2 - i2\zeta\omega_0\omega} \quad (5)$$

$$\omega_0^2 = \omega_d^2 + \gamma K_d P_0$$

$$\zeta = \zeta_d \omega_d / \omega_0$$

Figure 1B:
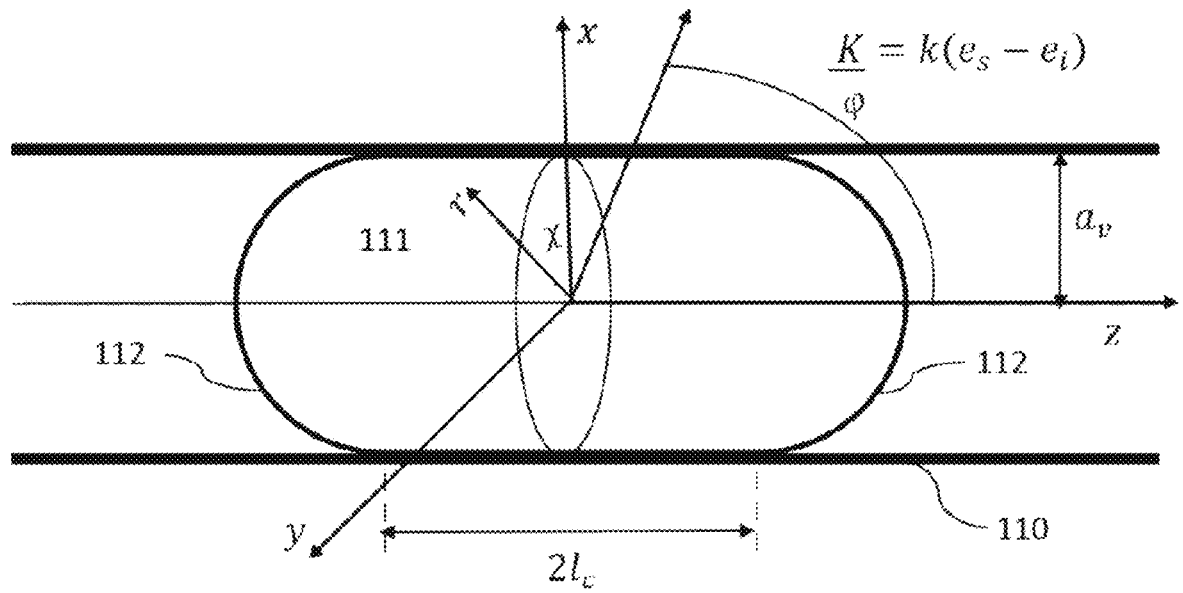
FIG. 1b Illustrates a micro-bubble filling a part of a capillary used to vibrate the capillary wall and extra capillary tissue FIG. 2a Illustrates interface vibration patterns of a capillary surface vibrated by a micro-bubble as shown in FIG. 1b.

For a bubble that partially fills a capillary with a large cylindrical region as 111 in FIG. 1b, the vibration pattern is more complex than the spherical vibrations behind the developments in Eqs. (2-5). The difference in material parameters across the vessel wall, i.e. between gas/tissue for the cylindrical bubble surface region ($S_c$), and blood/tissue for the blood surface region ($S_V$), produce interface waves along the vessel wall with propagation velocity $c_i \sim c_s$ in the vascular region and $c_i \sim 2c_s$ where the bubble contacts the vessel, as illustrated in FIG. 2a.

Figure 2A:
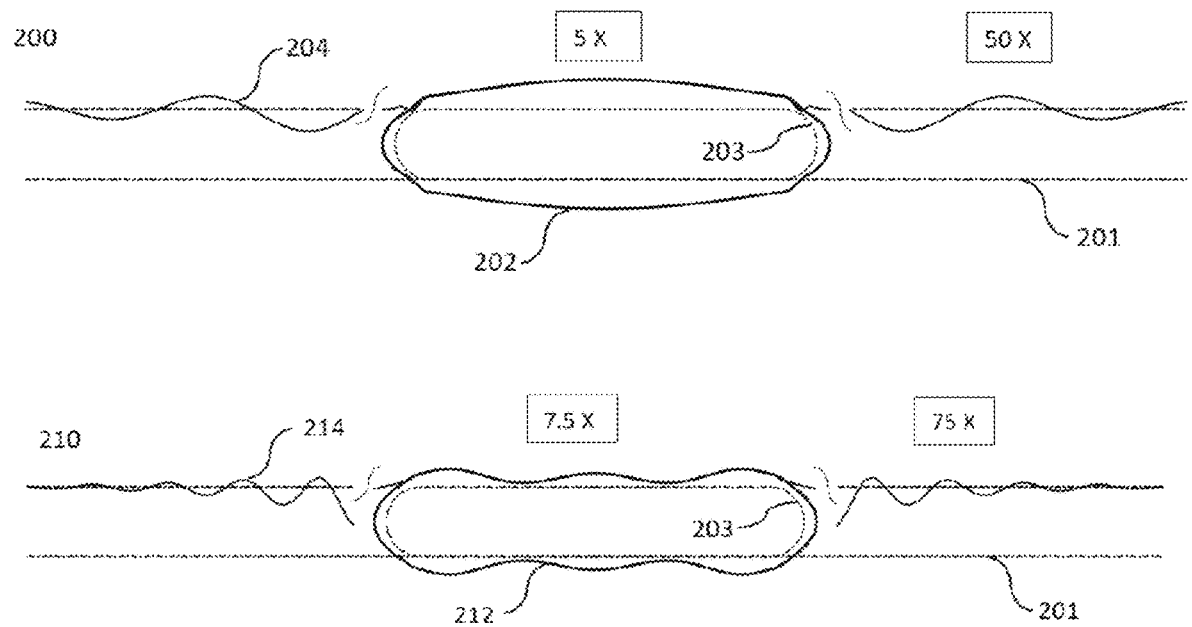
FIG. 2b Illustrates a numerical simulation of the displacement vibration amplitude as a function of position in the tissue surrounding the vibrating micro-bubble that fill s part of the capillary.

The FIG. 2a shows simulations of the spatial variation of the vibration amplitude of a bubble that fills part of a capillary (201 diam $2a_V = 10$ µm) together with interface waves along the blood/tissue interface outside the bubble. The upper panel 200 shows the vibration amplitudes at a frequency close to the volume vibration resonance, and the lower panel 210 shows a frequency 6 times the volume resonance frequency. At equilibrium the cylindrical part of the bubble fills the capillary and ends with the semi-spheres 203. Close to the resonance frequency in 200 the bubble surface amplitude 202 is magnified 5 times [5×] while the blood tissue interface wave amplitude 204 is magnified 50 times [50×]. At 6 times the resonance frequency in 210 the bubble surface amplitude 212 is magnified 7.5 times [7.5×] while the blood tissue interface wave amplitude 204 is magnified 75 times [75×] interface wave.

Figure 2B:
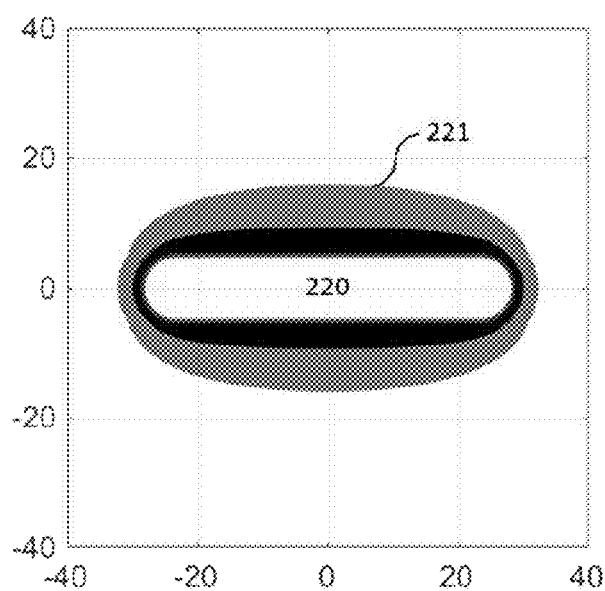

FIG. 2b gives as 221 a grey-scale display of the simulated tissue displacement amplitude around the bubble (220) close to the bubble volume resonance frequency. The volume amplitude can be expressed by the average normal vibration displacement amplitude across the bubble surface $S_b$ with area $A_b$ as $$\delta V_c = A_b \bar{\psi}_n \quad (6)$$

$$\bar{\psi}_n = \frac{1}{A_b} \int_{S_b} d^2 r_0 \psi_n(\underline{r}_0)$$

Eqs. (12,13,19) shows that for a bubble with dimensions adequately smaller than the incident wavelength the scattered signal is determined by the bubble volume $V_b$ and bubble volume compressibility $\kappa_b$. We note from FIG. 2b that the normal displacement amplitude on the semi-spherical ends is lower than the cylinder radial displacement amplitude, and these two observations stimulates an approximation of the bubble with cylindrical length $2l_b$ and semispherical ends of radius $a_V$, with a cylinder of fixed length 2L where the radius $a_V$ vibrates. The bubble volume $V_b$ for this cylindrical bubble is the same as for the original spherical bubble 101 in a large artery, and the bubble that fills part of a capillary in 111. We have the relation $$V_b = \frac{4}{3}\pi a^3 = \pi a_v^2 2l_c + \frac{4}{3}\pi a_v^3 = \pi a_v^2 2L \quad L = l_c + \frac{2}{3}a_v \quad (7)$$

$$\frac{l_c}{a_v} = \frac{2}{3}\left(\left(\frac{a}{a_v}\right)^3 - 1\right)$$

$$\frac{L}{a_v} = \frac{l_c}{a_v} + \frac{2}{3} = \frac{2}{3}\left(\frac{a}{a_v}\right)^3$$

where 2L is the length of a cylindrical bubble in a capillary with the same volume $V_b$. The vibrating area of the cylindrical bubble is $$A_c = 4\pi a_v L = 4\pi a_v l_c + \frac{8\pi}{3}a_v^2 = A_b - \frac{4\pi}{3}a_v^2 \quad (8)$$

We notice that Ac is $4\pi a_V^2/3$ which is ⅓ of the surface area of the end spheres. However, the effect of this error is reduced because the displacement of the semi-spherical end surfaces is less than the radial vibration of the cylinder surface as shown in FIG. 2b. We will therefore use the simplifying approximation $$\delta V_c = 2\pi a_v \int_{-L}^{L} dz \cdot \psi_r(\underline{r}_0) = A_c \bar{\psi}_r \quad (9)$$

$$\bar{\psi}_r = \frac{1}{2L}\int_{-L}^{L} dz \cdot \psi_r(\underline{r}_0)$$

$$A_c = 4\pi a_v L$$

Analysis of vibration and scattering from the cylindrical bubble is carried through in Appendix A. We note from 210 in FIG. 2a that at the higher frequency range we get multiple interface wave lengths along the bubble cylindrical surface which complicates the approximation with the $2^{nd}$ order transfer function in Eq. (5) over a larger frequency range. FIG. 3a shows as the solid lines a simulation of the magnitude $|H_V(\omega)|$ (300) and the phase $\theta_V(\omega) = \angle H_V(\omega)$ (301) of $H_V(\square)$ from Eq. (A10, A12) of Appendix A for $l_c/a_v = 5$. The dotted lines show the magnitude $|\hat{H}_V(\omega)|$ (302) and the phase $\hat{\theta}_V(\omega)$ (303) of the $2^{nd}$ order approximation $\hat{H}_V(\omega)$ of Eq. (A14). The approximation of the $2^{nd}$ order function to Eq. (A12) is done in the following steps:
1. $Re\{H_V(\omega_0)\}=0$ of Eq. (A14) gives the angular resonance frequency $\omega_0$.
2. $\zeta$ is determined from the differential of the ohase of $H_V$ as in Eq. (25).
3. $\omega_m$ and $K_V$ is determined from Eq. (27)

In the example in FIG. 3a we see that $f_0 \approx 340$ kHz and we can say that the approximation is very acceptable in a range larger than $\Omega_0 = 100\text{-}1000$ kHz$=(f_0/3, 3f_0)$.

To observe the LF vibration amplitude of a bubble driven by the incident LF wave with angular frequency $\omega_L$, the invention presents methods and instrumentation building on U.S. Pat. Nos. 8,550,998; 9,291,493; 9,939,413; 10,578,725 and 7,727,156; 10,879,867.

Figure 4:
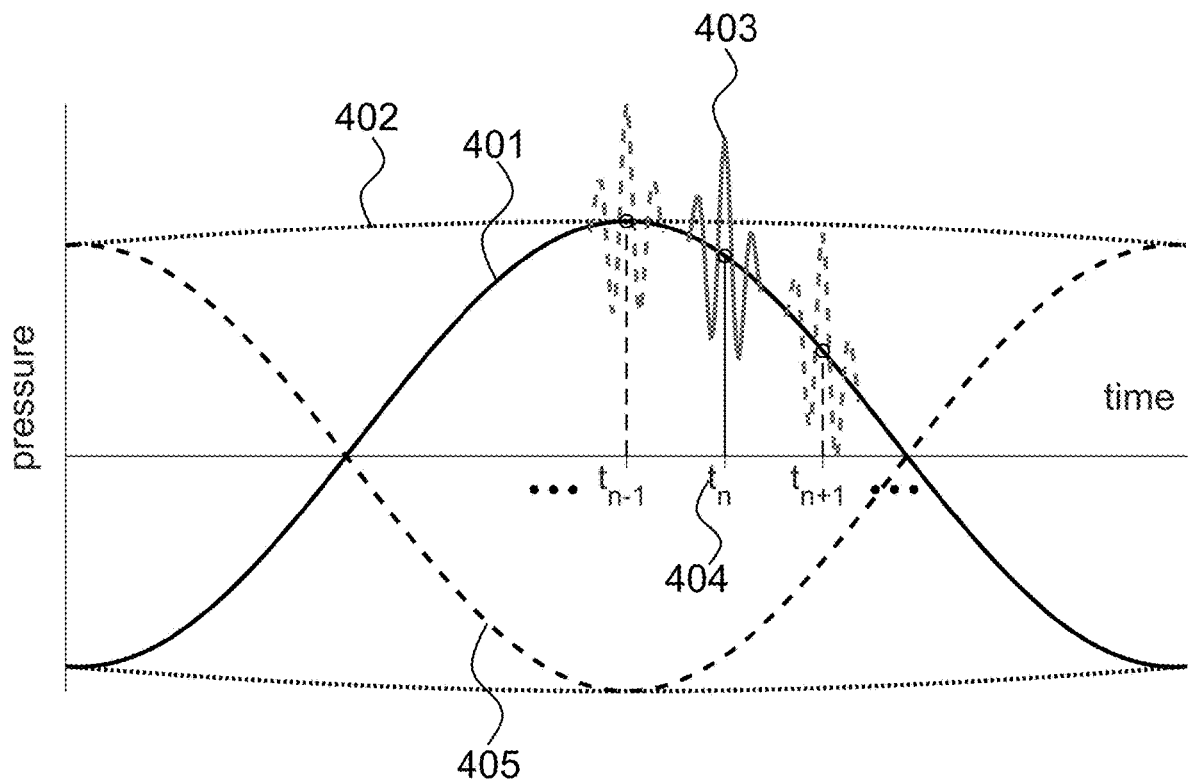
FIG. 4 illustrates two typical combined low frequency (LF) and high frequency (HF) ultrasound pulse complexes used to estimate the LF driven vibration amplitude and transfer function parameters of the micro-bubble.
Figure 5A:
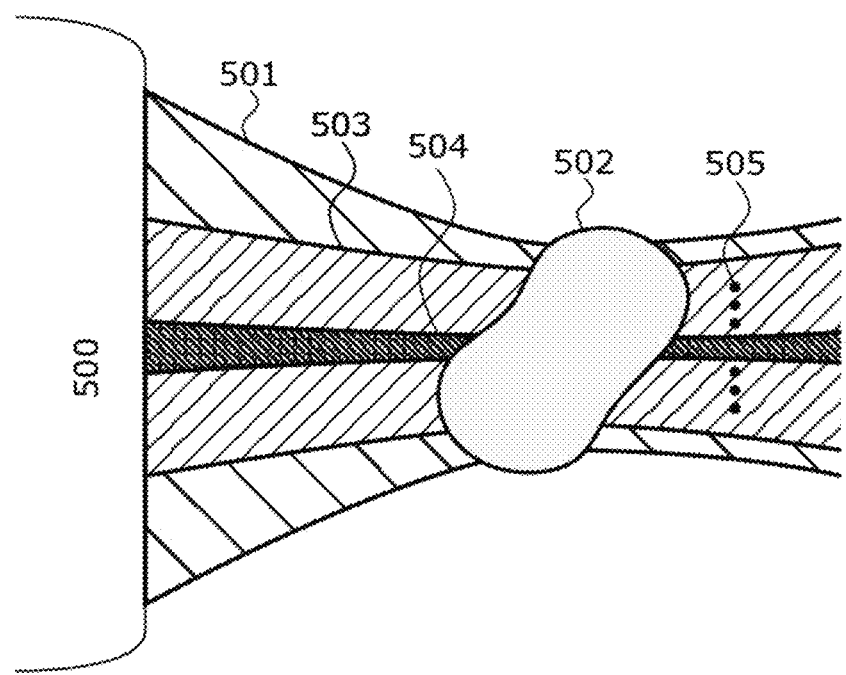
FIG. 5a-c Illustrates an ultrasound dual frequency array with LF transmit and HF transmit and receive beams typically used for identification of bubble vibration amplitude and tissue elastic properties.

An LF pulse shown by example as 401 or 405 in FIG. 4 is typically transmitted along an LF transmit beam (LT-beam) shown by example as 501 of FIGS. 5a and b, where 502 illustrates a therapy region. We have illustrated the LF transmit beam 501 with a large aperture and focused onto the therapy region 502 which allows higher LF pressure in the therapy region than in front of this region. For adequate therapy we want a certain surface displacement amplitude of the intra-capillary bubbles (FIG. 1b). For hard solid tumors, for example with large ingrowth of connective tissue and/or increased intra-tumoral pressure, adequate displacement amplitude requires increased LF pressure, e.g. 1 Mpa which gives an MI ~1.6 at LF ~400 kHz. This is seen as a risk MI for an intra-capillary contrast agent bubble with diam ~3 μm which could get excessive displacement collapse. However for a bubble that fills the capillary, the vibration displacement is more controlled by the surrounding tissue, and for the corresponding spherical bubbles in the larger arteries and arterioles the artery wall is much stronger so that dangerous damage is less likely. In the normal tissue in front of the tumor where the extra-capillary tissue has much lower shear stiffness, one should have lower LF pressure amplitude. The focused LF beam provides such spatial variation of the LF amplitude.

In many situations, for example trans-abdominal and trans-costal applications, the access window to the therapeutic region is limited, and it is desirable to have a HF transmit and receive beam arrangement with the same direction as the LF beam as illustrated in FIG. 5a, illustrated as 503 for the HF transmit beam and 504 for the HF receive beam. One would then typically use a wide HF transmit beam (503) with well multi-depth focused parallel HF receive beams 504 illustrated by the dots 505. Such multi-depth focusing is today obtained by software receive beam-formers utilizing parallel processing of Graphic Processing Units (GPUs). Hardware receive beamformers with such parallel receive beams also exists to-day.

Figure 5B:
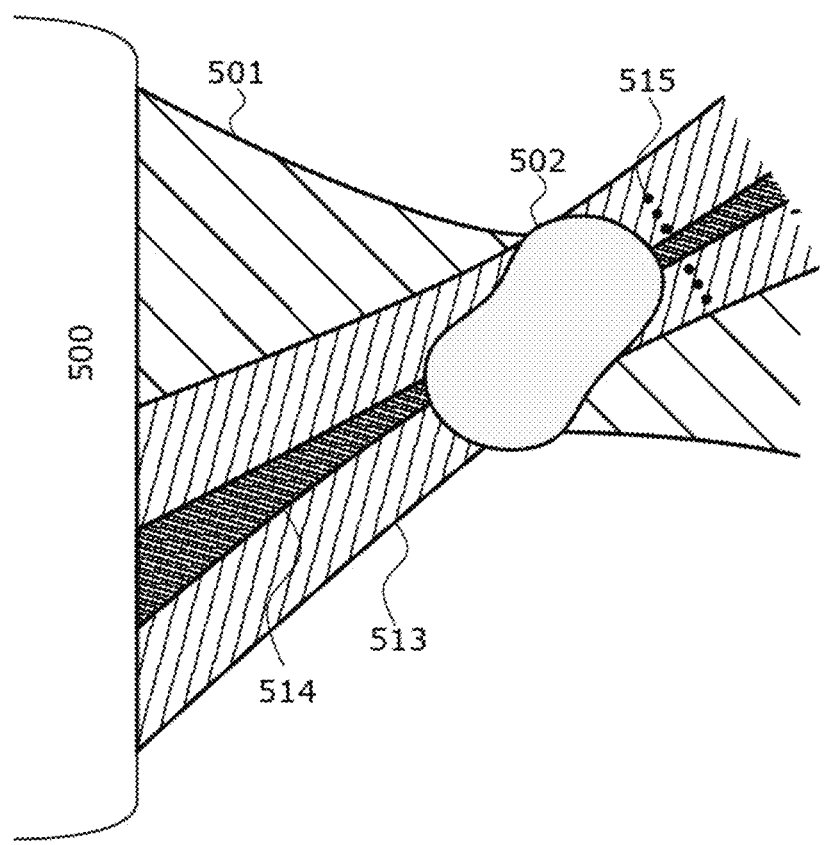

With adequate ultrasound access windows, it can be useful to use crossing multi/depth focused HF receive beams exemplified by 514 and the dots 515 in FIG. 5b, with the forward HF transmit beam as 503 in FIG. 5a. This reduces the length of the scattering wave vector $\underline{K}=k(\underline{e}_i-\underline{e}_s)$ as defined in Eq. (12). As discussed after Eq.(12) and in relation to FIG. 6a-d, this length reduction opens for the us higher HF frequencies with controlled reduction in the magnitude of $H_b$ and $\Delta H_b/H_b$ value produced by LF variation of the scatterer dimension.

In a particular solution, one transmits a set $S_N$ of $N \geq 1$ groups $G_n$ pulse complexes where one for each group $G_n$ transmits at least two pulse complexes comprising a LF manipulation pulse and a HF observation pulse where the LF pulse varies in one of amplitude, and polarity, and phase between each pulse complexes, where the LF pulse might be zero for one pulse complex, and the LF pulse is non-zero for at least one pulse complex. The LF pulses 401 and 405 in FIG. 4 are example LF pulses for two pulse complexes with opposite polarity of the LF pulses for one group $G_n$. The position of the HF pulse relative to the LF pulse is for the group $G_n$ defined by the timing $t_n$ of the HF pulse transmission. The timing varies between each group indicted by the time points . . . , $t_{n-1}$, $t_n$, $t_{n+1}$, . . . shown as 404 in FIG. 4. The envelopes of the LF pulses varies slowly and shown as 404 in FIG. 4. The HF is typically >~5*LF. The LF and the HF pulses can have different phase propagation with depth so that the positions $t_n$ of the HF pulses shown in FIG. 4 indicates the position of the HF pulses relative to the LF pulse at the depth of the bubble. This change in phase position can for example be obtained by numerical simulations of the combined LF and HF propagation to the bubble, or through measurements in a water or oil tank. For each group $G_n$ defined with position $t_n$ of the HF pulse, at least two pulse complexes are transmitted with different polarities and/or amplitudes of the LF pulse, where one LF pulse can have zero amplitude and at least one LF pulse has non-zero amplitude. In a preferred embodiment one transmits two pulse complexes with opposite polarities of the LF pulse shown as 401 and 405 in FIG. 4.

The time between transmit of the HF pulses is determined so that it is larger than the round trip propagation time $T_R$ from HF transmit transducer to the micro-bubble and to the HF receive transducer. In particular solutions where one wants long duration LF transmit vibration of the bubble we can use LF pulses with long duration time $T_L$, for example longer than $NT_R$ where N is the the number of groups $G_n$. Several groups $G_n$ of HF transmit pulses are then transmitted with time distance larger than $T_R$ and $t_n$ defining the detailed phase relation between the HF pulse and the LF oscillation of the bubble when the HF pulse hits the bubble.

Figure 5C:
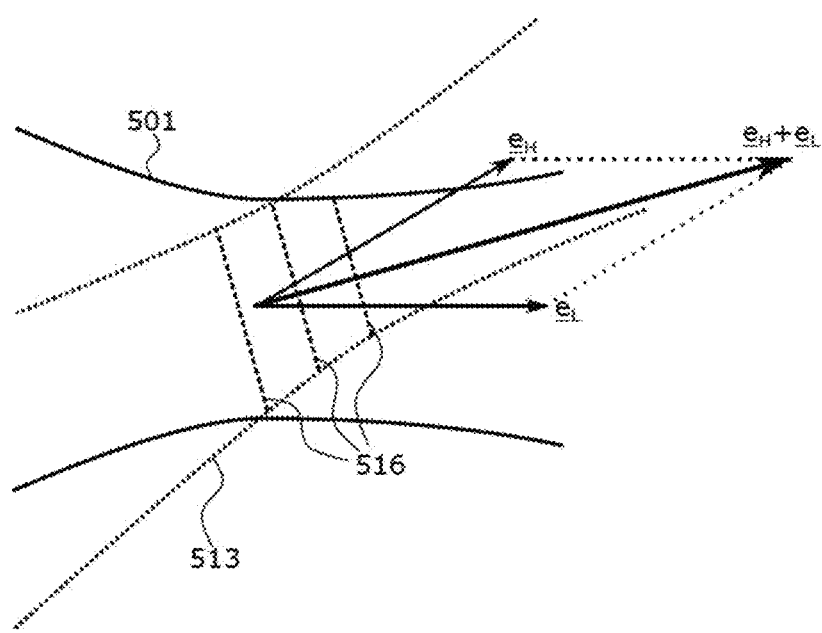

It is also interesting the use a HF transmit beam 513 that crosses the LF beam 501 in the same direction as the set of HF receive beams 514/515. FIG. 5c illustrates regions of constant phase relation between the HF and LF pulses in the case of crossing HF and LF transmit beams as in FIG. 5b, where said regions are along lines normal to the sum of the unit direction vectors of the HF and LF transmit beams. The advantage with the crossing HF transmit beam is that for a fixed phase transmit timing $t_n$ between the HF pulse and the phase of the LF oscillation, there will be a spatial variation of said phase relation through the therapy region, and there will be line regions exemplified by 516 in FIG. 5c along which said phase relation is constant. Said line regions have direction normal to $e_L+e_H$, where $e_L$ is the unit vector along the LF transmit beam axis and $e_H$ is the unit vector along the HF transmit beam axis. With adequate density of intra-capillary bubbles in the therapy region 502 there will be intra-capillary bubbles with adequate closeness to these line regions to produce the full amplitude of the bubble volume oscillation and full average bubble surface displacement amplitude $\bar{\psi}$ as defined in Eq. (9). Selecting the detection signal $D_{cm}$ according to Eqs. (18,20) from these bubbles with maximal $D_{cn}$ provides detection signals with the sought after phase relation between the HF pulses and the bubble vibrations when the HF pulses hits the bubble.

For therapy we generally drive the bubble with the low frequency (LF) pressure wave with angular frequency $\omega_L$, typically in the neighborhood of the bubble resonance frequency to produce large therapeutic cylindrical radius vibration amplitude (~1 μm). The LF pulse has an amplitude envelope $pP_{Le}(t)$, where p is a polarity parameter of the LF wave. p=1 implies positive LF amplitude (e.g. 401), p=−1 implies inverted LF amplitude (e.g. 405), while p=0 implies zero LF amplitude. Other values/sequences of the polarity parameter can be used to enhance the signal processing, where the cited patents show examples of p=0, ±1; p=±1, ±2, for example to improve suppression of tissue noise and/or compensate for bubble movements between the HF pulses.

The LF pulse produces a vibration in bubble volume as $$\zeta V_b(t, \omega_L) = p\delta V_{Le}(t)\cos[\omega_L t + \theta(\omega_L)]$$

$$\delta V_{Le}(t) \approx |H(\omega_L)| P_{Le}[t + \tau_e(\omega_L)] \approx |H(\omega_L)| P_{Le}(0) \quad (10)$$

Where $\theta(\omega_L) = \angle H(\omega_L)$ is the phase of $H(\omega_L)$, and $\tau_e(\omega_L) \approx \theta'(\omega_L)$ is an approximate delay of the envelope produced by the transfer function $H(\omega)$ for an adequately narrow band HF pulse. The last approximation of $\delta V_{Le}(t)$ assumes that he envelope varies slowly relative to the $\omega_L$ oscillation. To measure the bubble vibration amplitude we transmit HF observation pulses as described in FIG. 4. The bubble volume vibration when the HF pulse hits the bubble is then $$p\delta V_n = \delta V_b(t_n, \omega_L) = p\delta V_{Le}(t)\cos[\omega_L t_n + \theta(\omega_L)] \quad (11)$$

The scattered pressure field of an incident ultrasound pressure wave with angular frequency $\omega$ and amplitude $P_i$ from a bubble with volume $V_b$ and adequately less extension than the incident wavelength $\lambda$, is by the Born approximation obtained as $$p_s(\underline{r}, \omega) \approx k^2\left(\frac{\kappa_b(\omega)}{\kappa_t(\omega)} - \underline{e}_s \underline{e}_i\right) V_b H_b(\underline{K}) \frac{e^{-ikr}}{4\pi r} P_i \quad (12)$$

$$\kappa_b(\omega) = -\frac{1}{P_i}\frac{\delta V_b}{V_b} \quad \kappa_t(\omega) = -\frac{1}{P_i}\frac{\delta V_t}{V_t}$$

$$H_b(\underline{K}) = \frac{1}{V_b}\int_{V_b} d^3 r_0 e^{-i\underline{K}\underline{r}_0}$$

$$\underline{K} = \underline{k}_i - \underline{k}_s = k(\underline{e}_i - \underline{e}_s)$$

$$k = \frac{2\pi}{\lambda} = \frac{\omega}{c_p}$$

where
r is the radial distance from the bubble center of mass,
k is the wave vector magnitude of both the incident and scattered wave, and $\lambda = 2\pi/k$ is the wave length of both the incident and scattered waves.
$\underline{e}_i$ is the unit direction vector of the incident wave approximated as plane wave across the bubble with amplitude $P_i$,
$\underline{e}_s$ is the unit direction vector of the observed scattered wave,
$c_p$ is the pressure wave propagation velocity,
$\delta V_b$ is the vibration amplitude of the bubble volume, $V_b$, and
$\delta V_t$ is the vibration amplitude of the surrounding tissue volume, $V_t$, both produced by the incident wave,
$\kappa_b(\omega)$ is the bubble volume compressibility, and
$\kappa_t(\omega)$ is the volume compressibility of the surrounding material.

The term $\kappa_b/\kappa_t$ represents scattering due to the deviation of the bubble volume compressibility from the tissue volume compressibility, and the term $\underline{e}_s \underline{e}_i$ represents scattering due the relative difference between the bubble mass density ($\approx 0$) and the tissue mass density $\rho_t$. In a typical situation $|\kappa_b(\omega)/\kappa_t| \gg |\underline{e}_s \underline{e}_i|$, and the term $\underline{e}_s \underline{e}_i$ can be neglected. Using $c_p^2 = 1/\rho_t \kappa_t$ we modify Eq. (6) to $$p_s(\underline{r}, \omega) \approx \rho_t \omega^2 \kappa_b(\omega) V_b H_b(\underline{K}) \frac{e^{-ikr}}{4\pi r} P_i \quad (13)$$

$$\kappa_b(\omega) = -\frac{1}{P_i}\frac{\delta V_{cb}}{V_b} = H_V(\omega)$$

Both for contrast agent bubbles and bubbles for therapy, we are generally interested in vibrating the bubbles in the low frequency (LF) range $\Omega_0$ around the bubble volume vibration resonance frequency, where the $2^{nd}$ order transfer functions of Eqs. (5,A14) are useful. To measure the bubble vibration amplitude at $\omega_L$ we transmit in addition high frequency (HF) observation pulses with angular center frequency $\omega_H \sim 10\, \omega_L \gg \omega_0$ as illustrated in FIG. 4. We define this HF range as $\Omega_H$. The $2^{nd}$ order transfer function of Eq. (5) is still valid at $\omega_H$ for the spherical bubble in FIG. 1a. For the bubbles that fills part of a capillary in FIG. 1b one gets a multipolar variation of the bubble/tissue interface vibration amplitude $\psi_r(z, \omega)$, shown as 212 in FIG. 2a. We therefore use the transfer function $H_V$ given in Eqs. (A16,A17) to calculate the bubble volume compressibility $\kappa_b$ at $\omega_H \gg \omega_0$ for these bubbles. This gives different formulas for the spherical and the cylindrical bubbles as Spherical Bubble:

$$\kappa_b(\omega) \approx -\frac{K_d}{\omega^2} = -\frac{3}{\rho a^2 \omega^2} \quad (14)$$

$$p_s(\underline{r}, \omega) \approx -aH_b(\underline{K})\frac{e^{-ikr}}{r} P_i \quad Y_s(a; \omega) \sim aH_b(\underline{K})$$

Cylindrical Bubble: $\kappa_b(\omega) \approx -\dfrac{2K_d(L/a_v)}{\rho a_v^2 \omega^2} \quad (15)$ $$K_{pH}(L/a_v) = \frac{L}{a_v} K_d(L/a_v) = \frac{1}{\pi}\int dq \frac{qK_1(q)}{K_0(q)}\frac{\sin^2 qL/a_v}{q^2}$$

$$p_s(\underline{r}, \omega) \approx -a_v K_{pH}(L/a_v) H_b(\underline{K})\frac{e^{-ikr}}{r} P_i$$

$$Y_c(a_v; \omega) \sim a_v K_{pH}(L/a_v) H_b(\underline{K})$$

where it is shown the major dependencies of the receive signal Y (D;$\omega$) on the bubble dimensions D. For the spherical bubble D is the bubble radius a, while for the bubble filling parts of the capillary D is $(a_V, L)$ or $(a_V, a)$ by Eq.(7). A change in the bubble dimension/volume at the HF/LF time reference $t_m$ when the HF pulse hits the bubble, produces a change in the amplitude of the HF receive signal. For polarity p of the LF pulse the major change in bubble dimensions are Sphere: $\alpha = \alpha_0 + p\psi$ Cylindrical: $\alpha_V = \alpha_{v0} + p\overline{\psi}$ (16)

The spatial average $\overline{\psi}$ of the normal surface displacement is found for the cylinder as described in Eq. (9). The received signal from the HF pulse has angular frequency components in a band $\Omega_H$ centered around $\omega_H$. The propagation velocity $c_p$ of forward transmitted HF pulse observes a modification by the co-propagating LF wave as described in U.S. Pat. Nos. 9,291,493; 11,280,906; 11,275,006.

$$c_p = c_0(1 + p\beta P_L) \quad (17)$$

where $c_0$ is the low amplitude linear propagation velocity, $P_L$ is the pressure of the low frequency wave at the location of the HF pulse, $\beta$ is a nonlinearity parameter of the tissue bulk compression, and p is a scaling parameter defined in relation to Eqs. (10,11). This nonlinear propagation effect gives a non-linear propagation delay (NPD) to the HF pulse, $p\tau_n(r)$, and a weaker pulse form distortion (PFD) that increases with the propagation distance r is before scattering, as described in the cited patents. When the transmitted HF pulse is at the crest or through of the LF wave, the NPD has a larger effect than the PFD that generally can be neglected. When the transmitted HF pulse is at a zero crossing of the LF wave, the PFD has a larger effect than the NPD that generally can be neglected.

The back scattered HF signal will generally in addition to the scattering from the bubbles contain considerable scattering from tissue surrounding the bubble, and it is devised to suppress the tissue signal, for example by correcting the received signal for adequate NPD and/or PFD according to the methods in the cited patents, or using the $2^{nd}$ harmonic component of the received HF signal, or a combination of both. We notice, however that the transmitted LF amplitude to vibrate bubbles is generally lower than for imaging, and both the NPD and the PFD have less effect, and corrections for NPD and/or PFD can in many cases be neglected. Before further processing, we assume that the received HF signals are adequately corrected with the NPD and PFD, as described in the cited patents, and in the notation for the received HF signals below, we assume that that adequate correction have been done.

For illustration of a simplest form, we linearize the receive signals and form a detection signal $D_m$ with $p=\pm 1$ as $$Y_{np}(\omega) \approx Y_0(\omega) + p\delta Y_n(\omega) \quad (18)$$

$$\delta Y_n = \frac{\partial Y_n}{\partial a_v}\psi_n$$

$$D_n(\omega) = \frac{Y_{n-} - Y_{n+}}{Y_{n-} + Y_{n+}} = \frac{1}{Y_0}\frac{\partial Y_n}{\partial a_v}\psi_n$$

where the subscript n indicates the time point $t_n$ in FIG. 4 the measurements are done for, and the subscript n±implies p=±1. Other values for the polarity parameter p can be used as described in relation to FIG. 4 and Eqs. (10,11). We do in most of the equations operate in the angular frequency domain. As understood by any-one skilled in the art, Eq. (18) and other signal processing can through inverse Fourier transform be carried through in the time domain for a large range of depths.

Figure 6A:
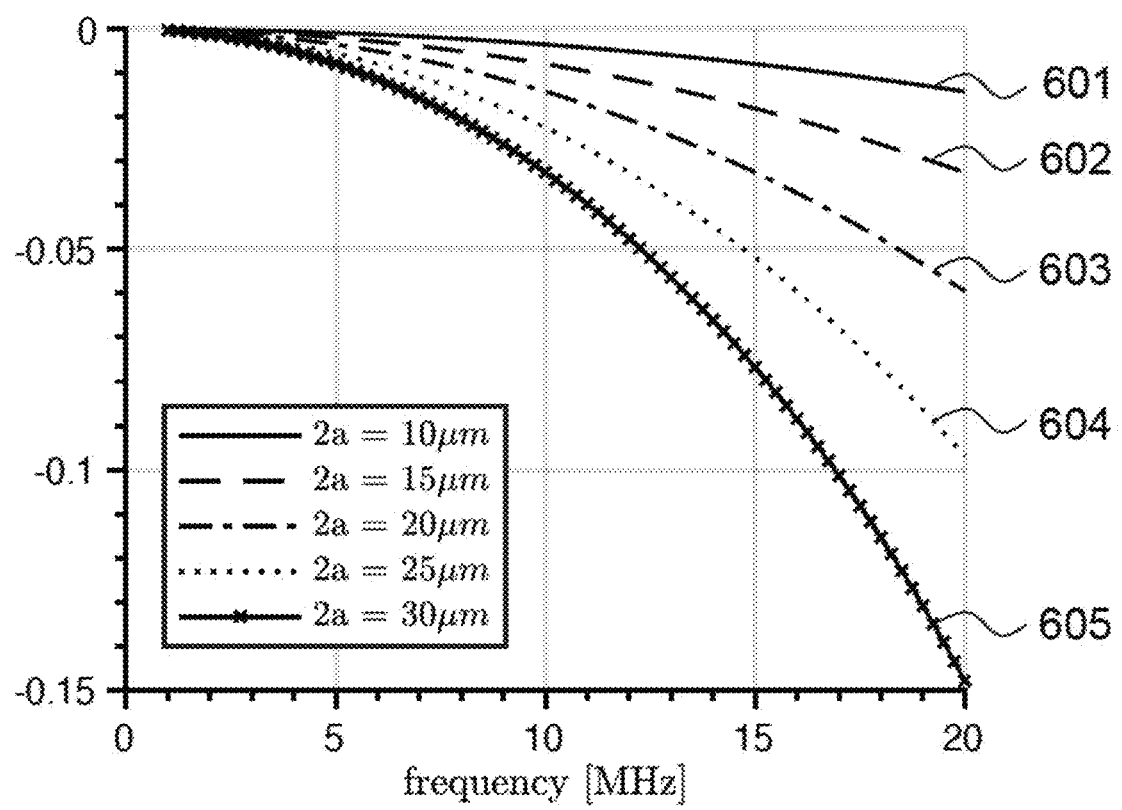
FIG. 6a Illustrates the variation of $H_b(\underline{K})$ for a spherical bubble as a function of frequency when the bubble diameter 2a becomes comparable to the incident wave length.

Components for $Y_s$ and $Y_c$ in Eqs. (14,15) that have low variation with bubble dimension variations are shorted in the ratio of $D_m$. In particular has $H_b$ low sensitivity to variations in bubble dimensions that are small compared to the wave length. $H_b(\underline{K})$ is the Fourier transform of the bubble volume with Fourier vector $\underline{K}=k(\underline{e}_i-\underline{e}_s)$. The largest magnitude $\underline{K}_{max}=2k\underline{e}_i=(4\pi/\lambda)\underline{e}_i$ is found for back-scattering where $\underline{e}_s=-\underline{e}_i$, which the situation in FIG. 5a where the HF transmit (503) and receive (504) beams have the same. With a HF receive cross beam as 514 in FIG. 5b and the HF transmit beam as 503 in FIG. 5a we get $K=k|\underline{e}_i-\underline{e}_s|<K_{max}=4\pi/\lambda$. For a spherical bubble we get We notice that for the sphere we have for back scattering $Ka=(4\pi a/c_p)\cdot f$ where f is the frequency and $c_p\approx 1500$ m/s is the propagation velocity of the pressure wave. FIG. 6a shows $\Delta H_b/H_b$ as a function of frequency for the spherical bubble where the curves 601, ..., 605 shows the curves for bubble diameters 2a=10, 15, 20, 25, 30 µm, and $\psi/a=0.1$. $\Delta H_b/H_{b0}<0.02$ is accepted as a tolerable error, which gives an upper frequency limit where $H_b$ can be accepted as a constant in the processing.

Figure 6B:
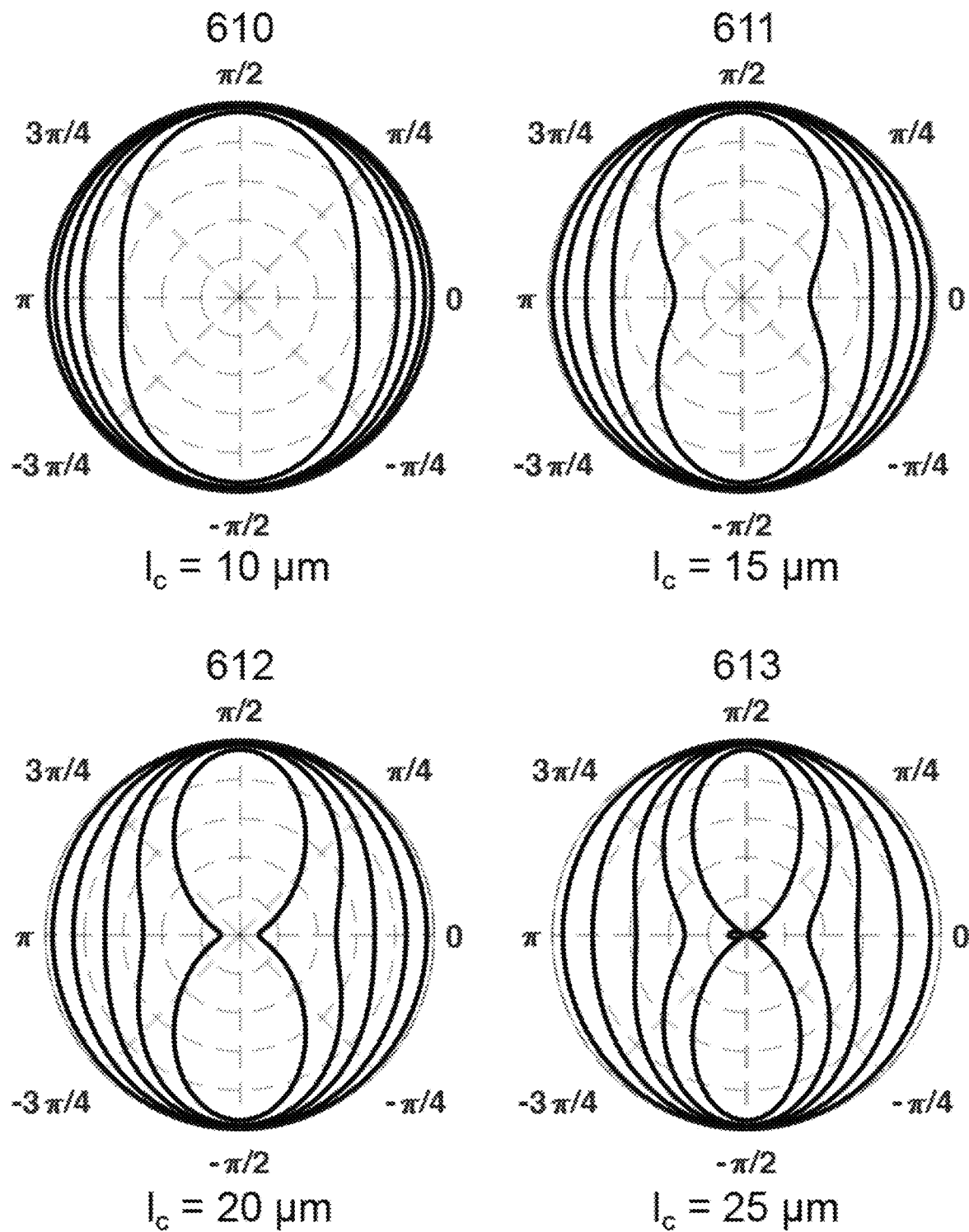
FIG. 6b-d Illustrates the variation of the $H_b(\underline{K})$ for a bubble that fills part of a capillary of radius $a_V=5$ μm as a function of angular direction and incident frequency for a cylindrical length $2l_c$.

Scattering from the cylindrical bubble in FIG. 1b gives more complex dependency of $H_b$ with bubble dimensions when the bubble long axis is larger than the capillary diameter. $H_b$ then becomes a function of both the short axis and long axis bubble dimensions, and the direction of $\underline{K}$ in relation to the bubble, for example described by the angle φ to the bubble long axis in FIG. 1b. FIG. 6b shows $H_b$ as a function of φ. The calculations are done for a capillary radius of $a_v=5$ µm, with a bubble cylindrical length $2l_c=20$ µm in 610, $2l_c=30$ µm in 610, $2l_c=40$ µm in 620, $2l_c=50$ µm in 630. Within each of the circular sub-figures we have a frequency from the outer to the inner curve of f=2.5, 5, 7.5, 10, 15 MHz in each of the Figures. We notice that for $\underline{K}$ normal to bubble long axis there is negligible change in $H_b$ in the actual frequency range, while for $\underline{K}$ along the bubble long axis the variation is much larger. To approximate $H_b$ to constant, we first must both have $H_b$ adequately large to get adequate signal in Eq. (14,15,18), while at the same time we must have $\Delta H_b/H_{b0}<0.025$ to assume $H_b$ constant.

Figure 6C:
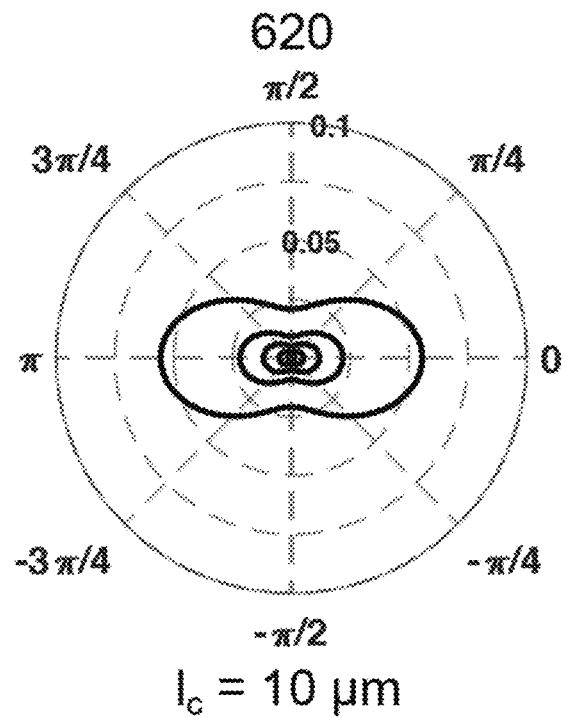
Figure 6C:
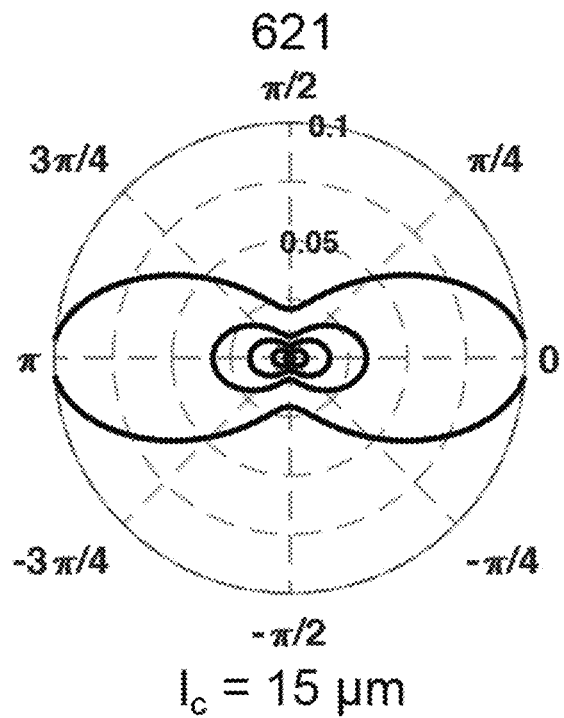
Figure 6C:
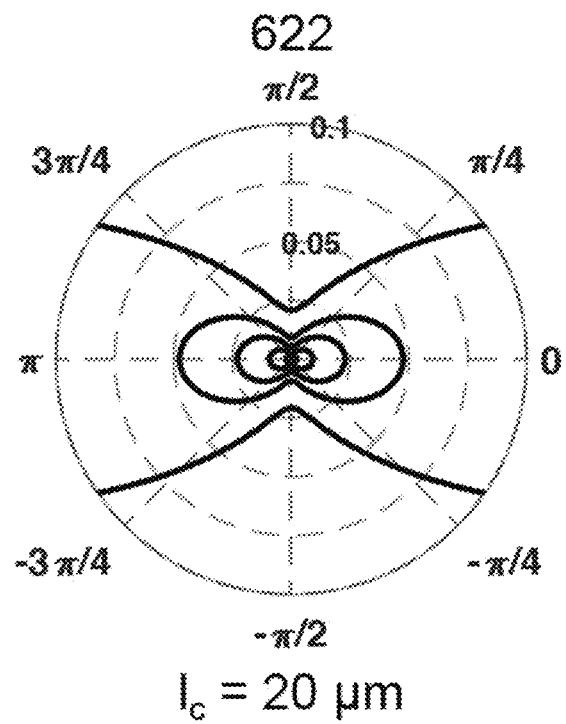
Figure 6C:
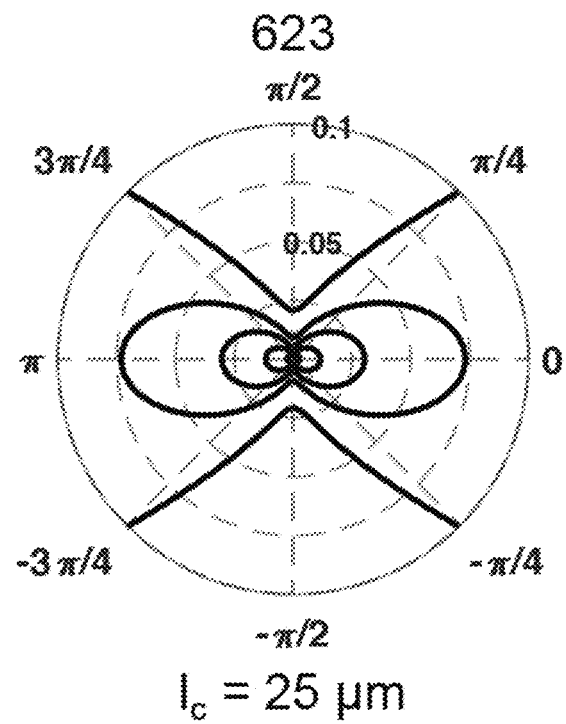

$\Delta H_b/H_{b0}$ is analyzed in FIG. 6c and d for the frequencies f=2.5, 5, 7.5, 10, 15 MHz that are displayed from the inner to the outer curve in each circular sub-figure. The capillary radius $a_v=5$ µm in all Figures, and the cylinder half-length $l_c$ is 10, 15, 20, 25 µm as listed under each circular sub-figure. FIG. 6c shows $\Delta H_b/H_{b0}$ for for $\Delta a_v=1$ µm, i.e. $\Delta a_v/a_v=0.2$.

Figure 6D:
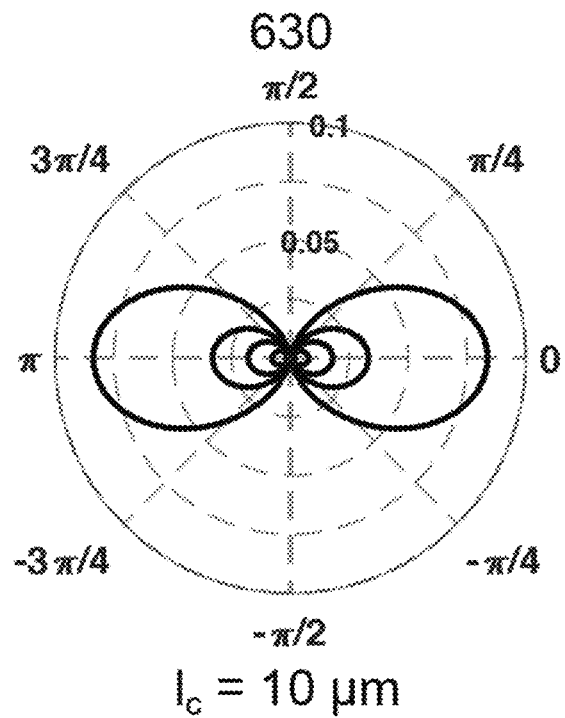
Figure 6D:
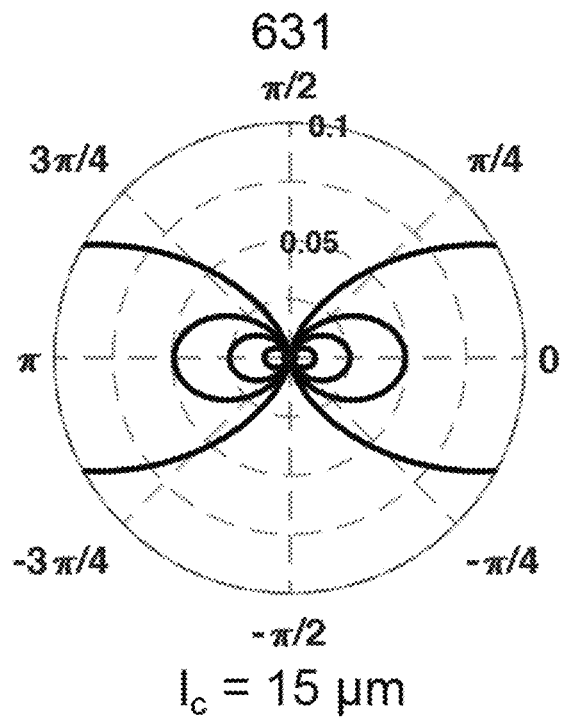
Figure 6D:
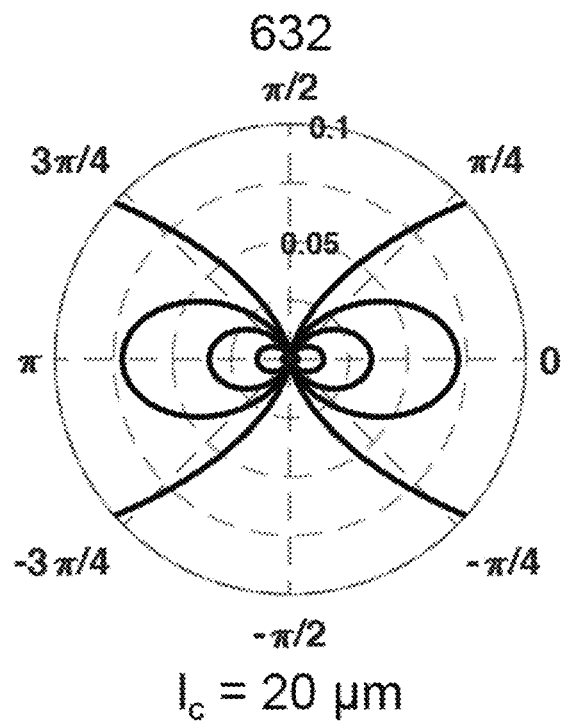
Figure 6D:
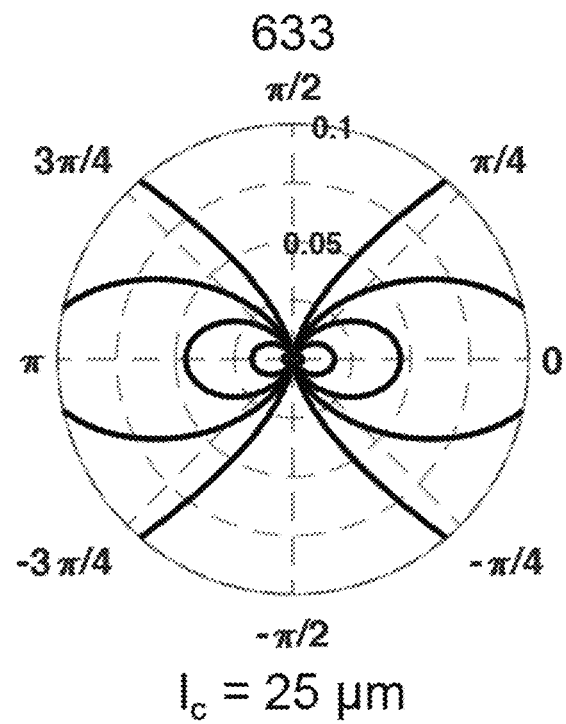

For this situation $\Delta H_b/H_{b0}<0.02$ is obtained for f=2.5 and 5 MHz. Reducing $\Delta a_v$ to 0.5 µm we have $\Delta H_b/H_{b0}<0.02$ up to 7.5 MHz for all situations. FIG. 6d shows $\Delta H_b/H_{b0}$ for $\Delta l_c=1$ µm for all values of $l_c$. For this situation $\Delta H_b/H_{b0}<0.02$ is obtained for f=2.5 and 5 MHz. Reducing $\Delta l_c$ to 0.5 µm we have $\Delta H_b/H_{b0}<0.02$ up to 7.5 MHz for all situations.

We expect capillaries and hence also bubbles to have random position within the tumor, and if we select the bubbles with the strongest back-scatter, i.e. incident wave normal to the capilary length and φ close to ±π/2 eg, we can assume that the variation of $H_b$ for the variations of the bubble dimension produced by the LF pulse is negligible for all the given bubble lengths and frequencies HF<15 MHz.

We note that when the incident HF beam hits close to the short axis of the bubble, both $H_{b0}$ and $\Delta H_\beta/H_{b0}$ are approximately independent of the dimension variations for HF<15 MHz When we can neglect the changes in $H_b$ with the bubble dimension variations produced by the polarity change in the incident LF pulse, $H_b$ is essentially canceled in the fraction of $D_m$ in Eq. (18). Neglecting $H_b$ in the expression for $Y_s$, $Y_c$ in Eq. (14,15) we see that $D_m$ of Eq. (18) gives $$\text{Spherical bubble: } H_b(\underline{K}) = \frac{3}{(Ka)^3}[\sin Ka - Ka\cos Ka] \quad \text{a)} \quad (19)$$

$$\text{Cylindrical bubble: } H_b(\underline{K}) = \frac{2\sin(KL\cos\varphi)}{KL\cos\varphi}\frac{J_1(Ka_v\sin\varphi)}{Ka_v\sin\varphi} \quad \text{b)}$$

$$\text{Spherical: } D_{sm} = \frac{Y_{sm-} - Y_{sm+}}{Y_{sm-} + Y_{sm+}} = \frac{\psi_{sm}}{a}, \quad \text{a)} \quad (20)$$

$$\text{Cylindrical: } D_{cm} = \frac{Y_{m-} - Y_{m+}}{Y_{m-} + Y_{m+}} = A_{cm}^{-1}\frac{\psi_{cm}}{a_v} \quad \text{b)}$$

Figure 7A:
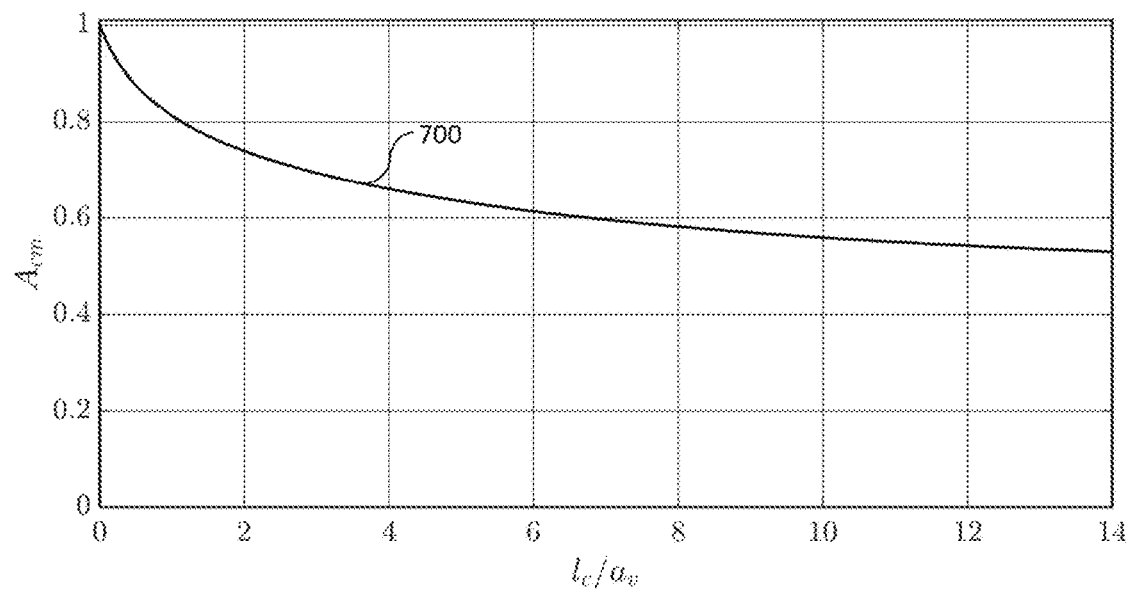
FIG. 7a Shows the detection sensitivity function of the average relative radial vibration amplitude for a bubble that fills part of a capillary with relative cylindrical half length $l_c/a_V$.

-continued $$\frac{\psi_{cm}}{a_v} = A_{cm} \frac{Y_{m-} - Y_{m+}}{Y_{m-} + Y_{m+}}$$

$$A_{cm}^{-1} \approx \frac{1}{K_{pH}(L/a_v)} \left( K_{pH}(L/a_v) + a_v \frac{\partial K_{pH}(L/a_v)}{\partial a_v} \right) \quad 5$$

where $K_{pH}(L/\alpha_v)$ is given in Eq. (15, A17). We note that $\psi_{cm}$ is the spatial average of the normal displacement $\psi_r$ for the cylinder, as shown in Eq.(A12), while $\psi_{sm}$ is the maximal displacement of the spherical bubble radius, as the bubble displacement is constant across the bubble surface. $A_{cm}$ as a function of $l_c/a_V$ is shown as 700 in FIG. 7a. The relation between L and $l_c$ is given in Eq. (7). We notice that for $l_c=0$ we have a sphere, and FIG. 7a shows $A_{cm}=1$, which is the value given for the sphere in Eq. (21a). This gives trust in the curve in the curve 700 for $A_{cm}$. Newly evaporated ACT bubbles have a cylindrical length $l_c/a_V \sim 3$- 20, depending on capillary radius and degree of gas absorption in the blood. The curve 700 shows that $A_{cm} \approx 0.55$-0.65 is a good assessment to obtain estimates of via, with interesting accuracy.

The relative volume variation $\delta V/V_b$ can be approximated from the relative displacement for the spherical and cylindrical bubbles with the linear approximations as $$\text{Spherical: } \frac{\delta V_s}{V_b} \approx 3\frac{\psi_{sm}}{a} \quad (21)$$

$$\text{Cylindrical: } \frac{\delta V_c}{V_b} \approx 2\frac{\psi_{cm}}{a}$$

Considering measurements errors and relative displacement magnitudes, these approximate expressions have good practical value. More accurate nonlinear expressions between $\delta V/V_b$ and the displacements can be calculated by anyone skilled in the art.

For the $2^{nd}$ order transfer functions in Eqs. (5,A14) it is possible to measure/estimate the three major parameters, $w_0$, $\zeta$, and $K_V$, for example in the following way. We get a phase estimate $\theta(\omega_L)=\angle H(\omega_L)$ of the transfer function at $\omega_L$ for the $t_n=t_m$ that gives maximum of $\zeta V_b$ in Eq. (11), i.e.

$$\omega_L t_m + \theta(\omega_L) = 0 \Rightarrow \theta(\omega_L) = -\omega_L t_m \quad (22)$$

Figure 7B:
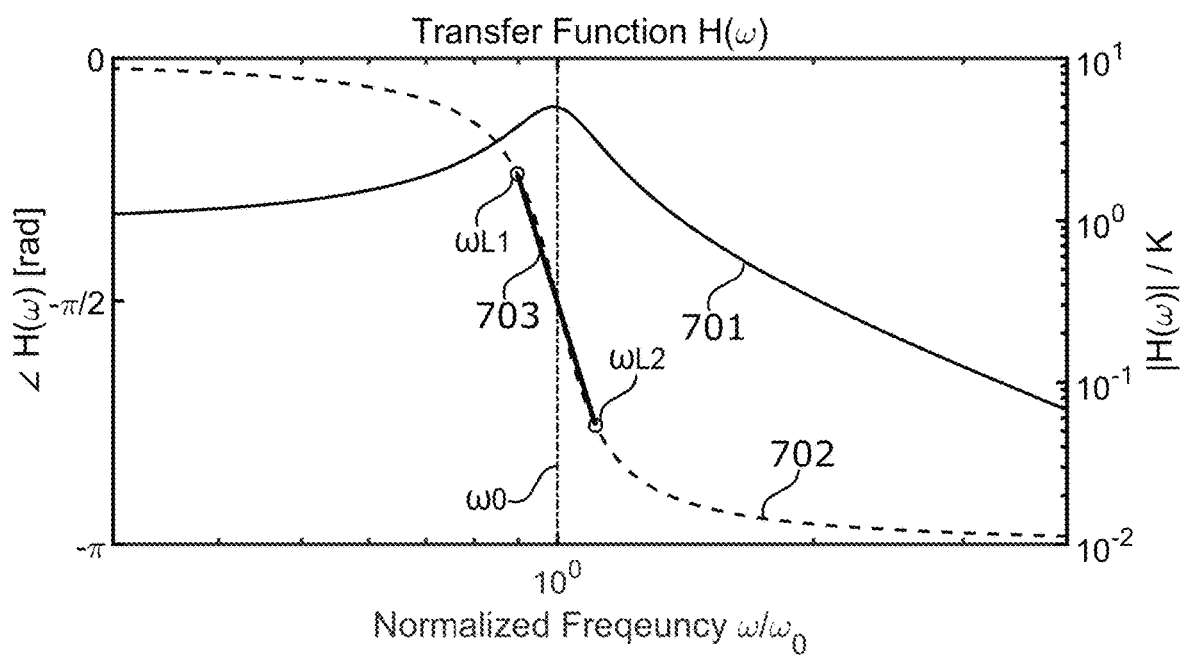
FIG. 7b illustrates the logarithmic amplitude and phase of a $2^{nd}$ order volume vibration transfer function in Eqs. (5, A14), with illustration of a linear approximation to parts of the phase function.

FIG. 7b shows an example amplitude (701) and phase (702) of the $2^{nd}$ order transfer function $H_V(\omega)$. Due to the − sign in front of $H_V(\omega)$ in Eqs. (5,A14) the resonance frequency $\omega_0$ the phase of the volume vibration amplitude $\delta V_{cb}(\omega)$ is $-\pi/2$ behind the driving pressure amplitude $-P_i$, while for $\omega$ adequately less than $\omega_0$ the phase-lag is $\approx 0$ behind $-P_i$, i.e. the vibration amplitude has close to opposite polarity of $P_i$. For $\omega$ adequately larger than $\omega_0$, the phase-lag is $\approx -\pi$ behind $-P_i$, i.e. the $\delta V_{cb}(\omega)$ has the same polarity as $P_i$. The amplitude and phase of the bubble vibration hence depend on the details of the transfer function (Gain K, resonance frequency $\omega_0$ and absorption $\zeta$).

Measuring $\hat{\theta}(\omega_{L1})$ and $\hat{\theta}(\omega_{L2})$ from Eq. (22) for two low frequencies $\omega_{L1}$ and $\omega_{L2}$ where we get the maximal detection signal for $t_{m1}$ and $t_{m2}$, we can for example though linear interpolation, indicated as 703 in FIG. 7b, write the phase variation between $\omega_{L1}$ and $\omega_{L2}$ as $$\hat{\theta}(\omega) = \hat{\theta}(\omega_{L1}) + \frac{\hat{\theta}(\omega_{L2}) - \hat{\theta}(\omega_{L1})}{\omega_{L2} - \omega_{L1}}(\omega - \omega_{L1}) \quad (23)$$

At the resonance frequency $\omega_0$ we shall have $\theta(\omega_0) = -\pi/2$ which gives an estimated resonance frequency from Eq. (23) as $$\hat{\omega}_0 = \omega_{L1} - \frac{\pi/2 + \hat{\theta}(\omega_{L1})}{\hat{\theta}(\omega_{L2}) - \hat{\theta}(\omega_{L1})}(\omega_{L2} - \omega_{L1}) \quad (24)$$

Matching the differential of the phase in Eq. (5,A14) at $\omega=\omega_0$ to Eq. (24) we get an estimate for the absorption losses in the tissue vibrations as $$\zeta = -\frac{1}{\omega_0 \theta'(\omega_0)} \Rightarrow \hat{\zeta} = \frac{\omega_{L2} - \omega_{L1}}{\hat{\omega}_0(\theta(\omega_{L2}) - \theta(\omega_{L1}))} \quad (25)$$

Another estimate of the absorption factor $\zeta$ is from Eq. (5) also found for a single low frequency $\omega_L$ as $$\hat{\zeta} = \frac{1}{2}\left(\frac{\omega_L}{\hat{\omega}_0} - \frac{\hat{\omega}_0}{\omega_L}\right)\tan\hat{\theta}(\omega_L) \quad (26)$$

The parameter $K_V$ can for example be found by the angular frequency $\omega_m$ that gives maximal amplitude of $H_V(\omega)$. From the estimates of $\hat{\omega}_0$ and $\hat{\zeta}$ and we can obtain an estimate of $$\hat{\omega}_m^2 = \hat{\omega}_0^2(1-2\hat{\zeta}^2) \quad \hat{K}_V = |H_V(\hat{\omega}_m)|\sqrt{\hat{\omega}_0^4 - \hat{\omega}_m^4} \quad (27)$$

where we measure $|H_V|$ at the estimated angular frequency $\omega_m$. If we do not have an estimate of $\hat{\zeta}$, we can search for the c that gives max $|H_V|$ and do the following calculations $$\hat{K}_V = |H_V(\hat{\omega}_m)|\sqrt{\hat{\omega}_0^4 - \hat{\omega}_m^4} \quad \hat{\zeta} = \sqrt{\frac{\omega_0^2 - \omega_m^2}{2\omega_0^2}} \quad (28)$$

Estimating the phases $\hat{\theta}_n = \hat{\theta}(\omega_{Ln})$ at more than two frequencies $\omega_{Ln}$, n=1, 2, . . . , N, we can improve the estimate of $\hat{\omega}_0$ with more complex interpolations, as known by any-one skilled in the art. By example, for n=1, . . . , N we the set of measured frequencies by the vector $\underline{\omega}_L = \{\omega_{L1}, \ldots, \omega_{Ln}, \ldots, \omega_{LN}\}$ and the set of estimated phases by $\underline{\theta}_L = \{\omega_{L1}, \ldots, \omega_{Ln}, \ldots, \omega_{LN}\}$, we can then form an estimate of $\hat{\omega}_0$ and $\hat{\zeta}\hat{\omega}_0$ through minimization of a mean square functional as $$J(\omega_0, \zeta; \underline{\omega}_L) = [\hat{\underline{\theta}}(\underline{\omega}_L) - \underline{\theta}(\omega_0; \zeta; \underline{\omega}_L)]^T [\hat{\underline{\theta}}(\underline{\omega}_L) - \underline{\theta}(\omega_0, \zeta; \underline{\omega}_L)] \quad (29)$$

$$(\hat{\omega}_0, \hat{\zeta}) = \min_{\omega_0, \zeta} J(\omega_0, \zeta; \underline{\omega}_L)$$

Other forms of functionals for minimization, also including added information, can be formed by any-one skilled in the art.

From Eq. (5-7) we notice that for $\hat{\theta}(\omega_L) + \omega_{L'm} \approx 0$ the amplitude of the received HF signal takes the form $$Y_{np} = Y_{n0} + p\delta Y_n - p|H_V(\omega_{Ln})|P_{Le}(t_n) \quad (30)$$

and we can for example include the amplitude of the received $\sim |H_V(\omega_{Ln})|$ for the different $\{\omega_{L1}, \ldots, \omega_{LN}\}$ in addition to the phase in the functional for parameter estimation in Eq. (29).

The extra capillary tissue is determined by the mass density, $\rho_t$, and the real and imaginary part, $\mu_{tr}$ and $\mu_{ti}$ of the complex shear stiffness of the tissue, as shown in Eq. (A6, A7). We can approximate $\rho_t \approx 1100$ kg/m³ for most solid tumor tissues, and hence it is $\mu_{tr}$ and $\mu_{ti}$ which are the most sought after tissue parameters. From the measured/estimated $\hat{\omega}_0$ and $\hat{K}_V$, we see from Eq. (A18) that we can obtain an estimate of $\hat{\omega}_d$ as $$\hat{\omega}_d = \sqrt{\hat{\omega}_0^2 - \gamma \hat{K}_V P_0} \quad \zeta_d = \frac{\omega_0}{\omega_d}\zeta \quad \hat{x}_d = \frac{\hat{\omega}_d}{\omega_s} \quad \omega_s = \frac{c_s}{a_v} = \frac{1}{a_v}\sqrt{\frac{\mu_{tr}}{\rho}} \quad (31)$$

where $\gamma \approx 1$ and $P_0 \approx 101$ kPa.

Figure 8A:
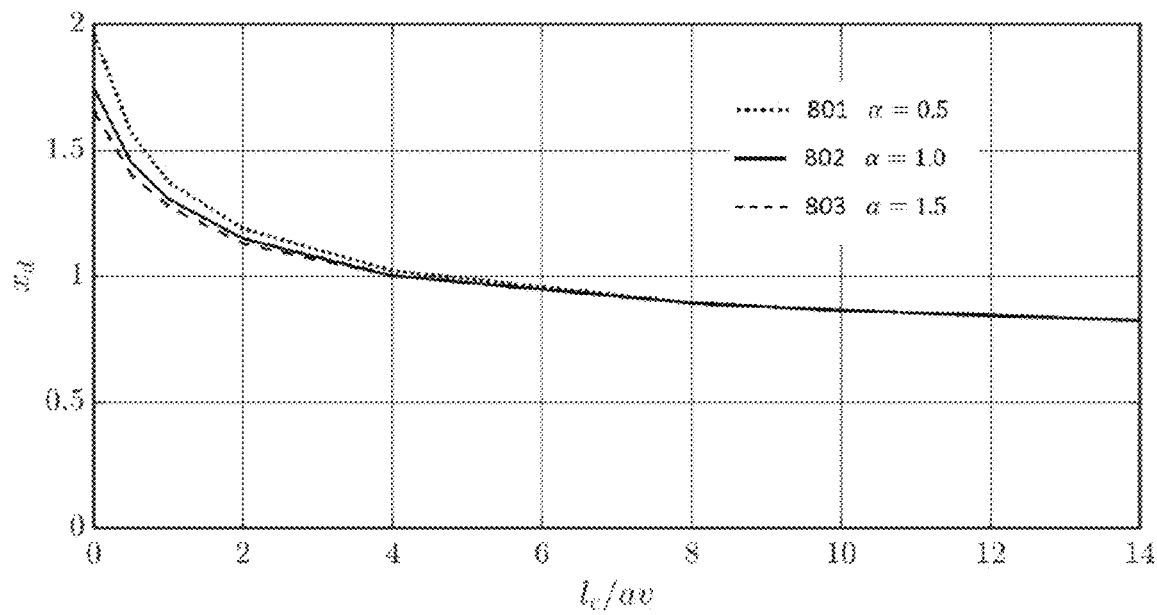
FIG. 8a Illustrates the variation of the relative resonance $x_d$ of the relative volume transfer function $F_d$ in Eq. (A11) as a function of relative cylindrical half length $l_c/a_V$ and 3 values of the tissue absorption parameter.

From $F_d(x)$ in Eq. (A11) we obtain estimated $x_d(l_c/a_V)$ from $\text{Re}\{F_d(x_d)\}=0$. FIG. 8a shows $x_d(l_c/a_V)$ for a set of absorption parameters $\alpha=0.5$, 1.0, 1.5, defined from $\eta=\mu_{ti}/\mu_{tr}=2\alpha x_d$. We notice that the variation of the curves with $\alpha$ Is barely visible, only for $l_c/a_V<4$. We also notice from Eq. (A10) that $\omega_s=c_s/a_V=\omega_d/x_d$ and $\mu_{tr}=\rho a_V^2\omega_s^2$ which allows us to calculate $$\frac{c_s}{a_v}(l_c/a_v) = \omega_s = \frac{\omega_d}{\hat{x}_d(l_c/a_v)} \quad \mu_{tr}(\omega_d) = \rho a_v^2 \frac{\omega_d^2}{\hat{x}_d^2(l_c/a_v)} \quad (32)$$

Figure 8B:
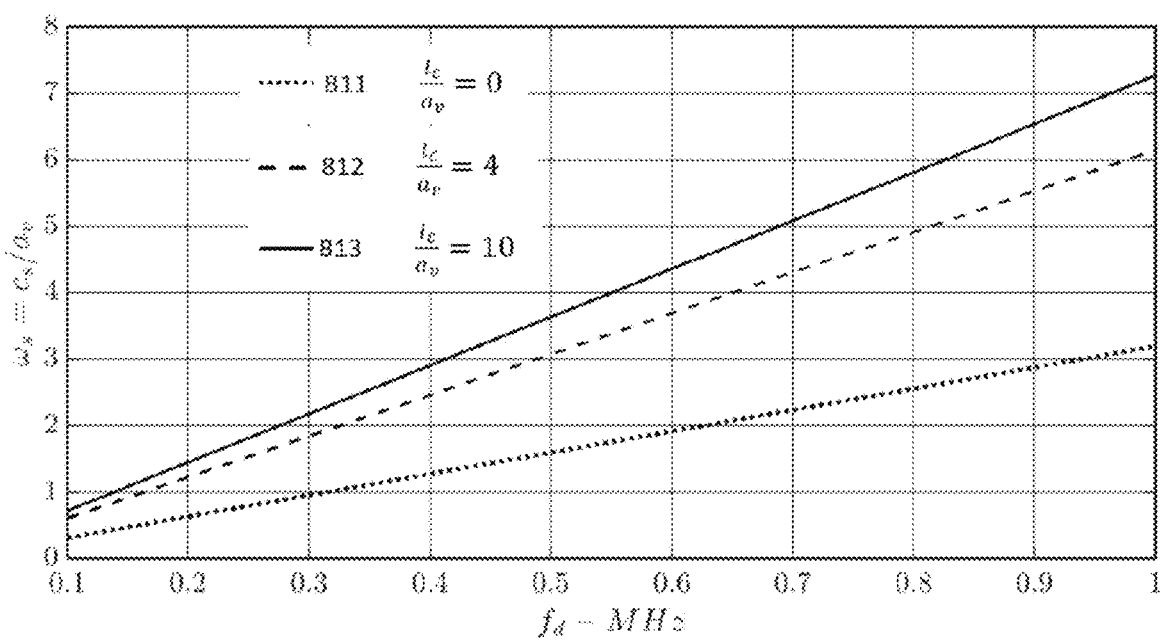
FIG. 8b Illustrates estimated ratio of the tissue shear wave velocity to the capillary radius, $c_s/a_V$, Eq. (32), as a function of observed bubble resonance frequency $f_d$.
Figure 8C:
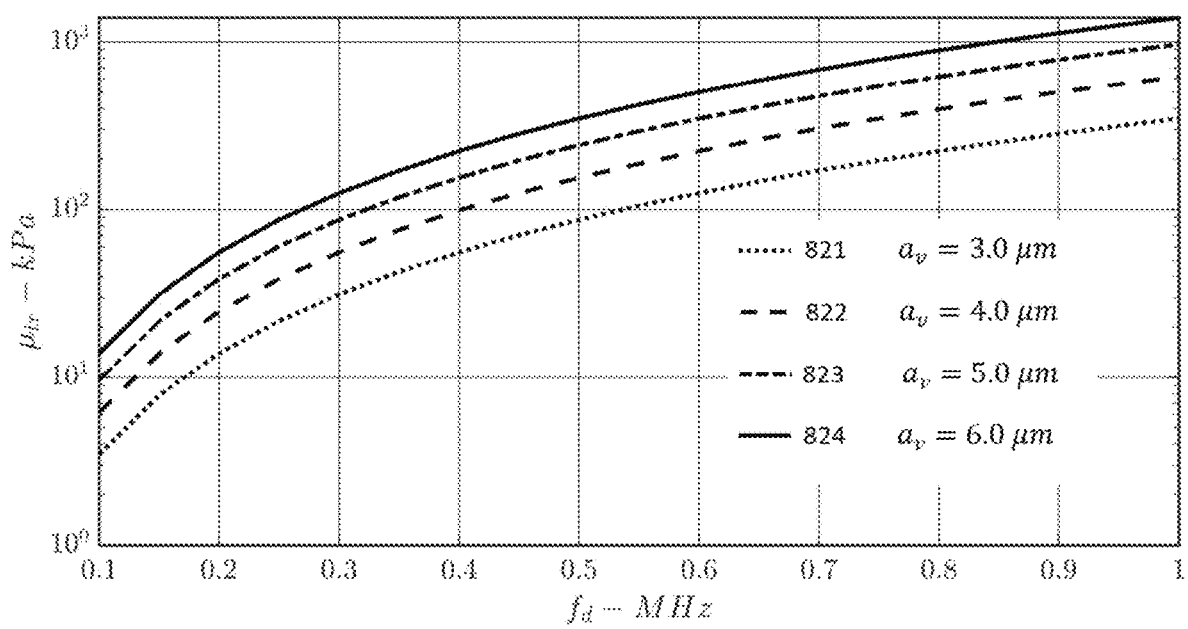
FIG. 8c Illustrates a logarithmic plot of the real component of the tissue shear stiffness as a function of observed bubble resonance frequency $f_d$ and 4 capillary radii.

FIG. 8b shows $\omega=c_s/a_V$ as a function of $\hat{\omega}_d$ for of $l_c/a_V=0$, 4, and 10 and FIG. 8c shows $\mu_{tr}(\omega_d)$ for $a_v=2, 4, 5,$ and 6 µm.

The power dissipated by the surface vibration at a surface area element $d^2r$ is $$dW = -\frac{1}{2}\text{Re}\{d^2 ri\omega\psi_n(\underline{r})^* P_i\} = -\frac{\omega}{2}\text{Im}\{d^2 r\psi_n(\underline{r})P_i\} \quad (33)$$

We assume $P_i$ approximately constant across the bubble surface, and integrated across the whole bubble surface gives the following power dissipation that provides a heating energy per unit time $$W = -\frac{\omega}{2}\text{Im}\left\{P_i\int d^2r\psi_n(\underline{r})\right\} = -\frac{\omega}{2}\text{Im}\{P_i\delta V_{cb}\} \quad (34)$$

Inserting the transfer function from Eq. (5), we get $$W(\omega) = \frac{\omega}{2}V_b P_i^2 \text{Im}\{H_V(\omega)\} = \frac{\omega_0\zeta K_V V_b \omega^2/\omega_0^2}{(1-\omega^2/\omega_0^2)^2 + 4\zeta^2\omega^2/\omega_0^2}P_i^2 \quad (35)$$

Hence, from estimation of $\omega_0$ and $\zeta$ and assessment of the bubble volume and the incident pressure amplitude, we can assess the dissipated power from the bubble on the surrounding tissue at $\omega=\omega_L$. Because $\omega_L$ is low, we can estimate the low frequency amplitude $P_i=P_L$ using an assessment of the low absorption. From the ultrasound image (2D or 3D) we can automatically estimate the number of bubbles N per unit volume and assess the total heat generation as $$W_T(\omega_L) = NW(\omega_L) \quad (36)$$

that can be used to estimate temperature increase in the tissue to avoid uncontrollable results.

FIG. 9 shows a block diagram of an example instrument for carrying out the methods according to the invention. 900 shows by example a 3D ultrasound probe comprising a dual frequency linear array 901 with a set of M LF elements and N HF elements in an azimuth direction indicated by the arrows 906. The dual frequency band linear array can be made according to known methods, for example as described in U.S. Pat. Nos. 7,727,156; 10,879,867. The LF and HF elements of the array are via a cable 902 connected to a transmit/receive unit 903 that connects each LF array element to LF transmit circuits, and each HF element to HF transmit/receive circuits comprising a HF transmit amplifier and a HF receive amplifier where the output of the HF receive amplifier is further connected to an analog to digital converter (A/D) presenting a digital representation of the HF received signals from all HF receive elements, according to known methods. The AD converter can in a modified embodiment present digital representations of the I-Q components of the HF receive signals from each HF element that represents the same information as the radio frequency (RF) HF signal, according to known methods. In a modified version of the instrument where one wants to receive the scattered LF pulse from the bubble, the LF elements are also connected to LF transmit/receive circuits.

For 3D scanning of the ultrasound beams, the linear array 901 can in this example embodiment be rotated around the long axis 904 that provides a mechanical scanning of the LF/HF beam in an elevation direction, indicated by the arrows 905. For each elevation position of the array, one does electronic scanning of LF/HF transmit beams in an azimuth direction indicated by the arrows 906, through electronic selection of transmitting LF and HF elements, and transmitting combined LF/HF pulse complexes for example as shown in FIG. 4, with selected beam directions and foci. An example HF transmit beam is illustrated schematically as 907 within a 2D azimuth plane 908 with given elevation position within a total 3D scan volume 909. Alternative elevation movements of the array, like side-ways movement can equivalently be done according to known methods, depending on the space available for such movement, and the shape of the object. Pure 2D scanning of the beam, and even measurements along a single beam direction is also within the scope of the invention. The array might also have a 2D matrix distribution of elements for 3D focusing and scanning of the beams, as known to anyone skilled in the art.

At least two pulse complexes with different LF pulses, for example as illustrated in FIG. 4, are transmitted for each transmit beam direction. The LF pulse might be zero in one pulse complex per HF transmit beam, but must be non/zero in at least one pulse complex for each HF transmit beam direction.

Two versions of the instrument are useful, where the first version 903 comprises beam former for HF receive cross-beams, illustrated as 914 in the 2D scan plane 908, and HF back scatter receive beams with the same axis as the HF transmit beam 907, shown in further detail in FIG. 5. In a preferred embodiment the HF back-scatter receive beam is equal to the HF transmit beam as this improves suppression of multiple scattering noise in the HF back-scatter receive signal, as discussed in U.S. Pat. Nos. 8,550,998; 9,291,493; 9,939,413; 10,578,725, and synthetic depth optimized focus is obtained through lateral filtering of the HF receive signals. During the scan, the HF cross-beam and back-scatter receive signals are via the high speed bus 910 transferred to the processor 911 for storage and further processing.

The processor 911 typically comprises at least one multicore central processing unit (CPU) and at least one graphics processor unit (GPU) that are SW programmable, according to known methods. The processor receives user inputs from a user/operator input unit 913 that operates according to known methods, and displays image data and other information necessary for communication with the user/operator through a combined display and audio unit 912, according to known methods.

In the second version of the instrument, the digital HF receive signals from each HF receive elements and each transmitted pulse complex are via the high-speed bus 910 transferred to the processor 911 for storage and further processing. For 2D imaging in the second version, a SW program in the processor unit 911 combines HF receive signals from multiple HF receive elements to produce both HF backscatter receive beams and HF receive cross-beams crossing each HF transmit beam in the 2D set, for example as shown as 914 and in more detail in FIGS. 5*b* and *c*. A set of HF back-scatter receive signals from HF back-scatter receive beams with the same axis as the HF transmit beams, and preferably also equal to the HF transmit beams 907, also shown in FIG. 5, can be produced by a software program.

One use of the cross-beam (914) HF receive signals is to estimate the nonlinear propagation delay at a multitude of depths along the HF transmit beam with low influence of multiple scattered noise, as described in US Pat Appl 2020/0405268. A set of cross beams is also useful to provide better suppression of signal from tissue, that is noise for detecting bubbles, vibration amplitudes, and tissue parameters. When we have imaging situations where the level of multiple scattering noise in the back-scatter HF receive signal is low compared to the 1st order scattered signals, the nonlinear propagation delay at multitude of depths along the HF transmit beam (907) can be obtained from the back-scatter HF receive signal, as described in the above cited US Patents, and the beam former for HF receive cross-beams, has less importance and can be omitted.

The processor 911 further comprises means, for example implemented as SW programs, to carry through the processing as described above to estimate
i) the relative variation of the bubble volume or displacement amplitude when driven by the LF signal, as for example described in Eqs. (19,21) and following equations, and
ii) the bubble vibration resonance frequency and absorption, as for example described in Eqs. (22-25, 30) and related equations, and
iii) parameters of shear elasticity of the extravascular tissue, for example as shown in FIGS. 8*b* and *c*.

The method and instrument is useful for estimating vibration amplitudes of bubbles of any dimension at an angular frequency we define as the low frequency, $\omega_L$. For spherical bubbles we have a good analytic relationship of a $2^{nd}$ order transfer function, Eq. (5) between the bubble radius and the scattered wave over a large frequency range from well below to well above the resonance frequency. For Bubbles that fill a capillary, like in FIG. 1*b*, we have in Appendix A develop an analytic expression for $H_V(w)$ in Eq. (A12) with an approximate $2^{nd}$ order transfer function for frequencies close to the volume resonance frequency in Eq. (A14). Eqs. (22-32) gives methods to identify the parameters of said model and the tissue surrounding a bubble that fills part of a capillary.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

APPENDIX A

For the vibration field outside the cylindrical capillary from the vibrating bubble in FIG. 1*b*, we use the cylindrical (r,z) coordinates as shown in the Figure. The incompressible field in the vabrating co-oscillating mass outside the capillary can for vibration of a cylindrical bubble with length 2L at an angular frequency $\omega$, be approximated by the Laplace equation for a potential $A(r,z;\omega)$ $$\nabla^2 A(r, z; \omega) + k^2 A(r, z; \omega) \xrightarrow[\lambda \gg 2L]{} \nabla^2 A(r, z; \omega) = 0 \quad (A1)$$

where $\lambda = 2\pi c_p/\omega$ is the wavelength of the pressure wave with propagation velocity $c_p$. The particle vibration displacement $\psi$ and the pressure P in the co-oscillating mass are obtained from A as $$\psi(r,z;\omega) = \nabla A(r,z;\omega) \quad P(r,z;\omega) = \rho\omega^2 A(r,z\omega) \quad (A2)$$

Fourier transform along the z-axis gives $$\frac{1}{r}\frac{\partial}{\partial r}\left(r\frac{\partial A(r, z)}{\partial r}\right) + \frac{\partial^2 A(r, z)}{\partial z^2} \xrightarrow{FT_z} \quad (A3)$$

$$\frac{\partial^2 A(r, k_z)}{\partial r^2} + \frac{1}{r}\frac{\partial A(r, k_z)}{\partial r} - k_z^2 A(r, k_z) = 0$$

Setting $x = k_z r$ and $A(r,k_z) = y(k_z r)$ we get the modified Bessel equation with the solution $K_0(x)$ $$x^2 y''(x) + xy'(x) - x^2 y(x) = 0 \quad x = k_z r \quad y(x) = K_0(x) \quad (A4)$$

With A defined for $r = a_V$ and a tissue mass density $\rho$, we get the following field amplitudes in the tissue outside the capillary $$A(r, k_z) = \frac{A_0(a_V, k_z)}{K_0(k_z a_V)} K_0(k_z r) \quad (A5)$$

$$P(r, k_z) = \rho\omega^2 A(r, k_z)$$

$$\psi_r(r, k_z) = \frac{\partial A(r, k_z)}{\partial r} = -k_z \frac{A(a_V, k_z)}{K_0(k_z a_V)} K_1(k_z r)$$

$$\psi_z(r, k_z) = -ik_z A(r, k_z) = -ik_z \frac{A(a_V, k_z)}{K_0(k_z a_V)} K_0(k_z r)$$

Inside the co-oscillating mass the incompressible tissue deformation produces shear stresses, which balances to zero inside the tissue, but at the boarder to the bubble at the capillary wall we get a stress contribution to the tissue surface as $$\sigma_{\mu r}(a_v, k_z) = 2\mu_t \frac{\partial \psi_r}{\partial r} = 2\mu_t \frac{\partial^2 A}{\partial r^2} = -2\mu_t \left( \frac{1}{r} \frac{\partial A}{\partial r} - k_z^2 A \right) \quad (A6)$$

$$\sigma_{\mu r}(a_v, k_z) = 2\mu_t \left( k_z^2 + \frac{k_z K_1(k_z a_v)}{a_v K_0(k_z a_v)} \right) A(a_v, k_z)$$

where $\mu_t = \mu_{tr} + i\mu_{ti} = \mu_{tr}(1+i\eta)$ is the complex shear stiffness of the tissue where the imaginary component produces absorption of oscillation power. At the bubble-tissue surface interface this stress adds to the pressure in Eq. (A5) to the following pressure from the cylindrical bubble surface towards the tissue $$P_d(a_v, k_z) = \rho\omega^2(a_v, k_z) - \sigma_{\mu r}(a_v, k_z) = \rho H_\omega(\omega; k_z a_v) A(a_v, k_z) \quad A(7)$$

$$H_\omega(\omega; k_z, a_v) = \omega^2 - 2\omega_c^2 \left( (k_z a_v)^2 + \frac{k_z a_v K_1(k_z a_v)}{K_0(k_z a_v)} \right)$$

$$\omega_c^2 = \frac{\mu_z}{\rho a_v^2} \quad \mu_t = \mu_{tr}(1-i\eta) \quad \omega_c^2 = \omega_s^2(1=i\eta) \quad \omega_s^2 = \frac{\mu_{tr}}{\rho a_v^2}$$

When the bubble cylindrical length $2l_c$ is adequately larger than the capillary radius $a_v$, we can approximate the bubble with semi-spherical end surfaces with radius $a_v$ with a cylinder with length 2L as shown in Eqs. (7, 8) above. $P_d(a_v, k_z)$ is the z-Fourier transform of a spatially constant drive pressure amplitude $P_d$ relative to infinity in the interval (−L, L), and zero outside $$P_d(a_v, k_z) = 2 \frac{\sin k_z L}{k_z} P_d \quad (A8)$$

$$A(a_v, k_z) = \frac{P_d(a_v, k_z)}{\rho H_\omega(\omega; k_z a_v)} = \frac{2}{\rho H_\omega(\omega; k_z a_v)} \frac{\sin k_z L}{k_z} P_d$$

$$\psi_r(a_v, k_z) = -\frac{k_z K_1(k_z a_v)}{K_0(k_z a_v)} A(a_v, k_z) = -\frac{k_z K_1(k_z a_v)}{K_0(k_z a_v)} \frac{2}{\rho H_\omega(\omega; k_z a_v)} \frac{\sin k_z L}{k_z} P_d$$

$$\psi_r(a_v, k_z) = -\frac{1}{2\pi} \int dk_z \frac{k_z K_1(k_z a_v)}{K_0(k_z a_v)} \frac{2}{\rho H_\omega(\omega; k_z a_v)} \frac{\sin k_z L}{k_z} e^{-ik_z z} P_d$$

The $\psi$ vibration amplitude at the cylindrical part of the bubble amplitude, gives a volume change of the cylinder $$\frac{\delta V_c}{V_b} = \frac{4\pi a_v L}{2\pi a_v^2 L} \frac{1}{2L} \int_{-L}^{L} dz \psi_r(a_v, z) = \quad (A9)$$

$$-\frac{2}{\rho a_v^2} \frac{1}{\pi} \int dk_z \frac{k_z K_1(k_z a_v)}{K_0(k_z a_v)} \frac{1}{H_\omega(\omega; k_z a_v)} \frac{\sin k_z L}{k_z^2 L} P_d$$

Changing integration coordinates $q = k_z \alpha_v$, $k_z = q/\alpha_v$, $dk_z = dq/\alpha_v$ we get the direct drive transfer function $H_d$ as $$\frac{\delta V_c}{V_b} = H_d(\omega; L/a_v) \frac{P_d}{\mu_{tr}} \quad (A10)$$

$$H_d(\omega; L/a_v) = -\frac{1}{\pi} \int dq \frac{q K_1(q)}{K_0(q)} \frac{2\omega_s^2}{H_\omega(\omega; q)} \frac{\sin^2 qL/a_v}{q^2 L/a_v}$$

$$\omega_s^2 = \frac{\mu_{tr}}{\rho a_v^2} = \frac{c_s^2}{a_v^2} \quad c_s^2 = \frac{\mu_{tr}}{\rho}$$

where $c_s$ is the shear wave velocity and $\omega_s$ is the shear wave angular frequency. Introducing $x = \omega/\omega_s$ we obtain the scaled direct drive transfer function $F_d$ as $$\frac{\delta V_c}{V_b} = F_d(x; L/a_v) \frac{P_d}{\mu_{tr}} \quad (A11)$$

$$F_d(x; L/a_v) = -\frac{1}{\pi} \int dq \frac{q K_1(q)}{K_0(q)} \frac{2}{H_x(x; q)} \frac{\sin^2 qL/a_v}{q^2 L/a_v}$$

$$H_x(x; q) = x^2 - 2[q^2 + q K_1(q)/K_0(q)](1+i\eta)$$

Note that for the cylindrical bubble in a capillary we have above put the surrounding tissue real shear stiffness $\mu_{tr}$ outside $H_d$ and $F_d$. This gives $F_d$ the nice property that it does not depend on $\mu_{tr}$ and $\omega_s$, only on $\eta$. We assume a linear variation $\eta$ with frequency, i.e. $\eta = 2\alpha x$. The resonance frequency of $F_d$ is defined as the value $x_d$ that equal zero, i.e. $\mathrm{Re}\{F_d(x_d; L/a_v\}$. FIG. 3b shows $x_d(l_c/a_v)$ as a gives the real part of $F_d$ function of $l_c/a_v$. The angular resonance frequency of $H_d$ is $\omega_d = \omega_s x_d$. The variation of $x_d$ with $l_c/a_v$ is quite low and we can approximate $x_d \approx 1$ for $l_c/a_v$ in the range 1 to 8. This allows us to approximate the direct drive resonance function $\omega_d \approx \omega_s$. For $l_c/a_v = 0$ we get the direct drive values for the spherical bubble that touches the capillary wall at one circle as $x_d \approx 1.7$-2 for the absorption $\alpha = 0.5$-1.5 and $\omega_d \approx (1.7$-2$)\omega_s$. The resonance frequency for a spherical bubble that is fully confined in soft tissue is $\omega_d \approx 2\omega_s$. The value for a spherical confined in blood with the short touch to the capillary wall does not seem a bad estimate.

Including gas elasticity according to Eq. (3) we get the complete transfer function from incident pressure to relative volume amplitude $$\frac{\delta V_c}{V_b} = H_d(\omega; L/a_v) \frac{P_d}{\mu_{tr}} = -H_v(\omega; L/a_v) P_i \quad (A12)$$

$$H_v(\omega; L/a_v) = \frac{H_d(\omega; L/a_v)/\mu_{tr}}{1 - \gamma H_d(\omega; L/a_v) P_0/\mu_{tr}}$$

Figure 3:
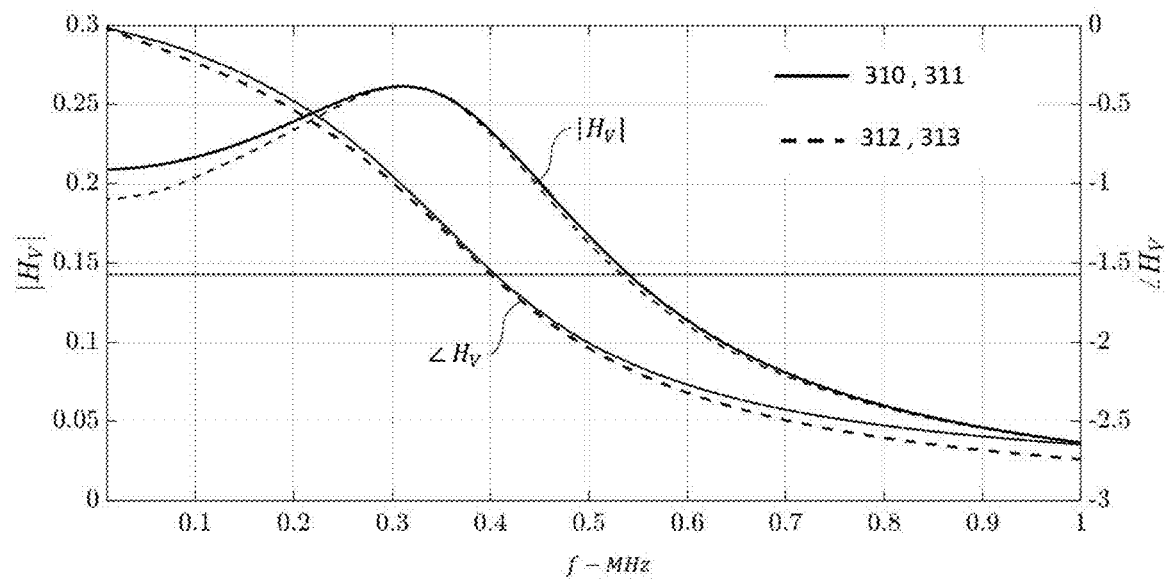
FIG. 3 Illustrates approximation of a 2nd order transfer function Eq. (5, A14) to the transfer function in Eq. (A12) from incident wave amplitude $P_i$ at a frequency f to the bubble volume complex vibration amplitude.

FIG. 3 shows that we for a practical interval around the resonance frequency can approximate the transfer function with a $2^{nd}$ order transfer function with $\omega_d = \omega_s X_d$ $$\hat{F}_d(x; L/a_v) \approx \frac{-K_F}{x^2 - x_d^2 - i2\zeta_d x_d x} \quad (A13)$$

$$\hat{H}_d(\omega; L/a_v) \approx \frac{-K_d}{\omega^2 - \omega_d^2 - i2\zeta_d \omega_d \omega}$$

$$\omega_d^2 = \omega_s^2 x_d^2 \quad K_d = \omega_s^2 K_F$$

Due to the frequency variation of the displacement along the bubble surface as shown in 212 of FIG. 2a, $K_F$ has to be adapted numerically, for example so that the maximal amplitude of the $F_d$ approximation in Eq. (A13) matches to the maximal amplitude in Eq. (A11). From Eq. (A12) we see that with a given incident amplitude $P_i$ we can include the variations in the gas pressure on the bubble volume to get the complete $2^{nd}$ order transfer function as $$\hat{H}_V(\omega;L/a_v) = \frac{\hat{H}_d(\omega;L/a_v)/\mu_{tr}}{1-\gamma\hat{H}_d(\omega;L/a_v)P_0/\mu_{tr}} = \frac{-K_V}{\omega^2-\omega_0^2-i2\zeta\omega_0\omega} \quad (A14)$$

$$K_V = \frac{K_d}{\mu_{tr}} = \frac{K_F}{\rho a_v^2}$$

$$\omega_0^2 = \omega_d^2 + \gamma K_v P_0 = \omega_s^2(x_d^2 + K_F(L/a_v)P_0/\mu_{tr})$$

$$\zeta = \zeta_d\omega/\omega_0 \quad K_V = \omega_s^2 K_F/\mu_{tr}$$

With the $2^{nd}$ order approximation of $H_V$ in Eq. (A14) we can from Eq. (13) approximate the scattered field in the low frequency range as $$\kappa_b(\omega) = -\frac{1}{P_i}\frac{\delta V_{cb}}{V_b} = H_v(\omega) \quad (A15)$$

$$p_s(\underline{r},\omega) = -H_p(\omega)H_b(\underline{K})\frac{e^{-ikr}}{r}P_i$$

$$H_p(\omega) = \frac{K_{pL}\omega^2}{\omega^2-\omega_0^2-i2\zeta\omega_0\omega}$$

$$K_{pL} = \frac{1}{2}\rho_t a_v^2 LK_V = \frac{1}{2}LK_F = \frac{1}{2\omega_s^2}LK_d$$

For detection of the low frequency LF vibration amplitude we transmit a high frequency (HF) pulse, HF ~10*LF or more, i.e. $\omega \gg \omega_0$, as described in relation to Eqs. (12-19) and FIG. 4. Eq. (A12) includes these HF variations of the bubble surface displacement amplitude as illustrated in 212. We can then approximate the bubble volume compressibility from Eq. (A12) for $\omega \gg \omega_0$ $$\kappa_b(\omega) = \quad (A16)$$

$$H_V(\omega)\frac{1}{\mu_{tr}} \approx H_d(\omega)\mu_{tr} \approx -\frac{2K_d(L/a_v)\omega_s^2}{\omega^2}\mu_{tr} = -\frac{2}{\rho a_v^2\omega^2}K_d(L/a_v)$$

$$K_d(L/a_v) = \frac{1}{\pi}\int dq \frac{qK_1(q)}{K_0(q)}\frac{\sin^2 qL/a_v}{q^2 L/a_v}$$

Inserted into Eq. (13) we then get the approximation to the scattered field for the $\Omega_H$ frequency range as $$p_s(\underline{r},\omega) \approx -a_v K_{pH}(L/a_v)H_b(\underline{K})\frac{e^{-ikr}}{r}P_i \quad (A17)$$

$$K_{pH}(L/a_v) = \frac{L}{a_v}K_d(L/a_v) = \frac{1}{\pi}\int dq \frac{qK_1(q)}{K_0(q)}\frac{\sin^2 qL/a_v}{q^2}$$

The received HF amplitude is then proportional to $$Y_r(a_v,L,\underline{K}) \sim a_v K_{pH}(L/a_v)H_b(\underline{K}) \quad (A18)$$

With the $2^{nd}$ order approximation of $H_V$ in Eq. (A14) the angular frequency $\omega_m$ for max $|H_V(\omega)|$ is given by $$\zeta = -\frac{1}{\omega_0 \theta'(\omega_0)} \quad (A19)$$

$$\omega_m = \omega_0\sqrt{1-2\zeta^2}$$

$$\zeta = \sqrt{\frac{\omega_0^2-\omega_m^2}{2\omega_0^2}} \quad |H_V(\omega_m)| = \frac{K_V}{\sqrt{\omega_0^4-\omega_m^4}} \quad K_V = \frac{K_d}{\mu_{tr}} = \frac{K_F}{\rho a_v^2}$$

REFERENCES

1. Lars Hoff: "Acoustic Characterization of Contrast Agents for Medical Ultrasound Imaging" Springer Science+ Business Media. 2001

What is claimed is:

1. A method for estimating parameters related to the surface or volume displacement vibration amplitude of at least one micro-bubble brought to vibration by an ultrasound wave of amplitude $P_L$ and angular frequency $\omega_L$ transmitted along a LF beam with a given propagation direction along the unit vector $\underline{e}_L$, comprising
   a) transmitting towards said at least one micro-bubble at least two high frequency (HF) pulses with $\omega_H > 5\omega_L$ along one HF beam along the unit vector $\underline{e}_H$ at different times,
   b) directing at least one HF receive beam towards the region of the at least one micro-bubble with a direction $\underline{e}_{HR}$, the LF transmit and the HF transmit and receive beams are arranged so that they overlap at least in an observation region that includes said at least one micro-bubble,
   c) arranging the transmit timing of each of the transmitted HF pulses so that the pulses hits said at least one micro-bubble at different phases the LF oscillation,
   d) receiving at least two HF receive signals scattered from each said at least two transmitted HF pulses, and
   e) processing the at least two HF receive signals, to for each said at least one micro-bubble to produce an estimate of a bubble vibration parameter that gives one or both of the relative vibration of one or both of i) the bubble volume vibration relative to the resting bubble volume, and ii) a parameter related to relative bubble volume vibration
   wherein
      the HF transmit beam is directed in close to the same direction as the LF transmit beam and the LF transmit and HF transmit and HF receive beams are positioned so that the three beams overlap in a region around said at least one micro-bubble, to produce estimates of said bubble vibration parameter for each said at least one micro-bubble;
      a set $S_N$ of $N \geq 1$ groups $G_n$ of combined LF and HF pulse complexes are transmitted, each group $G_n$ comprising at least two pulse complexes, where for each group the LF pulse amplitude can be zero for one pulse complex, and the LF pulse amplitude is non-zero for at least one pulse complex, and at least one of the polarity, amplitude, or phase of the LF pulse varies between pulse complexes,
      for each group $G_n$ the HF pulse is transmitted with a timing relative $t_n$ to the LF pulse so that the HF pulses hit said at least one micro-bubble with a phase relation of $\omega_L t_n$ relative to the transmitted LF oscillation, where the time $t_n$ is different for different groups $G_n$, the processing includes combining the HF receive signals from the scattered HF pulses from said at least two HF transmit pulses for each group $G_n$ to produce a detection parameter $D_n$ for group $G_n$ and each said at least one micro-bubble, and for each said at least one micro-bubble, the detection parameter Dm for the group Gm that gives maximal detection parameter for all $G_n \cdot S_N$ is used as an estimate to obtain an estimate of the amplitude of said bubble vibration parameter.

2. The method according to claim 1, where the HF receive signals are compensated by one or both of i) a nonlinear propagation delay, and ii) a nonlinear pulse form distortion in the processing chain to produce estimates of said bubble vibration parameter for each said at least one micro-bubble.

3. The method according to claim 1, for an adequately dense group of micro bubbles, where
   a) the HF transmit beam defined by $\underline{e}_H$, is directed at an angle to the direction of the LF transmit beam defined by $\underline{e}_L$, and
   b) at least one HF receive beam are positioned together with the LF and HF transmit beams so that the three beams overlap at the region of said dense group of micro-bubbles, and
   c) transmitting a single group $G_n$ comprising at least two HF pulses at a reference time $t_n$, and one of
   ci) the LF pulse polarity is switched between at least two of the HF pulses within the group, and cii) internal timing of the pulses within the group is selected, so that at least two HF pulse complexes hits at least one bubble within said group of micro-bubbles at opposite polarities of the LF oscillation, and
   d) processing that includes combining the received HF signal from said at least two HF pulses to produce a detection parameter $D_n$ for each bubble n in said group of micro-bubbles, and
   e) selecting estimate of a bubble vibration parameter the detection parameter $D_m$ for the bubble n=m that has the highest value.

4. The method according to claim 1, where said parameter related to relative bubble volume vibration is the average surface normal vibration amplitude relative to a radius of the bubble.

5. The method according to claim 4, where the value of the average surface normal is used to set the transmit amplitude of the LF wave.

6. The method according to claim 1, where the LF beam is focused onto in the therapeutic region.

7. The method according to claim 1, where the HF beam is broad with width less than the LF beam in the observation region, and several multi-focused parallel HF receive beams are generated to provide spatial resolution in the estimates of said bubble vibration parameter for a group of micro-bubbles.

8. The method according to claim 1, where scanning in 2 or 3 dimensions of one or more of
   i) the HF receive beam direction, and
   ii) the HF transmit beam direction, and
   iii) the LF beam direction
   to produce images of vibrating micro bubbles and the vibration amplitudes of the bubbles for a given transmitted amplitude of the LF wave.

9. The method according to claim 1, where the phase of the $2^{nd}$ order transfer function between incident LF pressure oscillation and the amplitude bubble volume vibration is estimated from the timing $t_m$ that gives the maximal detection parameter $D_m$.

10. The method according to claim 9, where the maximal detection parameter $D_m$ is obtained for at least two different frequencies of the LF beam, and estimates of the following parameters of the $2^{nd}$ order approximation to the transfer function from incident pressure amplitude to bubble volume vibration
   i) the angular resonance frequency $\hat{\omega}_0$ of the bubble
   ii) the absorption coefficient $\hat{\zeta}$ of the $2^{nd}$ order approximation to the incident LF pressure to bubble volume transfer function,
   iii) the gain $\hat{K}_V$ of the $2^{nd}$ order approximation to the incident LF pressure to bubble volume transfer function.

11. The method according to claim 10, where for a bubble filling parts of a vessel estimates of at least one of the following vibration parameters for the surrounding tissue is obtained
   i) the ratio of the tissue shear wave velocity $c_s$ to the vessel radius $a_V$ is obtained from the estimate of the angular resonance frequency $\hat{\omega}_0$ of the bubble,
   ii) for a known radius of the vessel the real part of tissue shear stiffness is obtained from the estimate of the angular resonance frequency $\hat{\omega}_0$ of the bubble,
   iii) for a known radius of the vessel the imaginary part of tissue shear stiffness is obtained from the estimate of the angular resonance frequency $\hat{\omega}_0$ of the bubble.

12. An instrument for obtaining estimates of parameters related to the surface or volume displacement vibration amplitude of at least one micro-bubble brought to vibration by an ultrasound wave of amplitude $P_L$ and angular frequency $\omega_L$, comprising
   a) means for transmitting towards said at least one micro-bubble
      ai) at least one LF pulse along a LF transmit beam with a transmit beam direction along a unit vector $\underline{e}_L$, and
      aii) at least two high frequency (HF) pulses with $\omega_H > 5\omega_L$ along a HF beam along the unit vector $\underline{e}_H$ at different times, and
      iii) means for arranging the transmit timing of each of the transmitted HF pulses so that the pulses hit said at least one micro-bubble at different phases the LF oscillation,
   said means for transmitting include means for transmitting said HF transmit beam in close to the same direction as the LF transmit beam and further includes
      i) means for transmitting a set $S_N$ of $N \geq 1$ groups $G_n$ of combined LF and HF pulse complexes, each group $G_n$ comprising at least two pulse complexes, where for each group the LF pulse amplitude can be zero for one pulse complex, and the LF pulse amplitude is non-zero for at least one pulse complex, and ii) means for varying at least one of the polarity, amplitude, or phase of the LF pulse between pulse complexes, and iii) means that for group $G_n$ for sets the transmit time $t_n$ of the HF pulse relative to the LF pulse so that the HF pulses hit said at least one micro-bubble with a phase relation of $\omega_L t_n$ relative to the LF pulse oscillation when the HF pulse hits the at least one micro-bubble, where the time $t_n$ is different for different groups $G_n$ and
   b) means for receiving that includes include means for directing the HF receive beam so that the LF transmit and HF transmit and HF receive beams overlap at the position of said at least one micro-bubble and further including i) means for directing at least one HF receive beam with direction $\underline{e}_{HR}$ to produce an overlap region (OR) with the LF and HF transmit beams that includes the at least one micro-bubble, and ii) means for receiving at least two HF receive signals scattered from each said at least one micro-bubble from said at least two transmitted HF pulses, and c) means for processing the at least two HF receive signals, to for each said at least one micro-bubble to produce an estimate of a bubble vibration parameter that gives one or both of the relative vibration of one or both of i) the bubble volume vibration relative to the resting bubble volume, and ii) a parameter related to relative bubble volume vibration, wherein said means for processing includes i) means for combining the scattered HF pulses from said at least two HF pulses for each group $G_n$ to produce a detection parameter $D_n$ for group $G_n$ and each said at least one micro-bubble, and ii) means for selecting for each said at least one micro-bubble, the detection parameter $D_m$ for the group $G_m$, that gives maximal detection parameter for all $G_n \cdot S_N$, said $D_m$ is used as a basis to obtain an estimate of the amplitude of said bubble vibration parameter.

13. The instrument according to claim 12, where said processing means include means for compensating the HF receive signals by one or both of i) a nonlinear propagation delay, and ii) a nonlinear pulse form distortion in the processing chain to produce estimates of said bubble vibration parameter for each said at least one micro-bubble.

14. The instrument according to claim 12, for an adequately dense group of micro bubbles, where a) said means for transmitting includes ai) means for directing the HF transmit beam defined by $\underline{e}_H$, at an angle to the direction of the LF transmit beam defined by $\underline{e}_L$, and aii) means for transmitting a single group $G_n$ comprising at least two HF pulses at a reference time $t_n$, and one of a) the LF pulse polarity is switched between at least two of the HF pulses within the group, and ii) internal timing of the pulses within the group is selected, so that at least two HF pulse complexes hits at least one bubble within said group of micro-bubbles at opposite polarities of the LF oscillation, and b) said means for receiving includes means for directing at least one HF receive beam together with the LF and HF transmit beams so that the three beams overlap at a region of said dense group of micro-bubbles, and c) said means for processing includes ci) means combining the received HF signal from said at least two HF pulses to produce a detection parameter $D_n$ for each bubble n in said group of micro-bubbles, and cii) means for selecting the detection parameter $D_m$ for the bubble n=m that has the highest value, and use $D_m$ in the processing chain to produce and estimate of a bubble vibration parameter.

15. The instrument according to claim 12, where the LF beam is focused onto in the therapeutic region.

16. The instrument according to claim 12, where the HF transmit beam is broad with width less than the LF beam in the observation region, and several multi-focused parallel HF receive beams are generated to provide spatial resolution in the estimates of said bubble vibration parameter for a group of micro-bubbles.

17. The instrument according to claim 12, where said parameter related to relative bubble volume vibration is the average surface normal vibration amplitude relative to a radius of the bubble.

18. The instrument according to claim 17, comprising means to use the value of the average surface normal to set the transmit amplitude of the LF wave.

19. The instrument according to claim 12, where said transmit and receive means comprises means for scanning in 2 or 3 dimensions of one or more of i) the HF receive beam direction, and ii) the HF transmit beam direction, and iii) the LF beam direction to produce images of vibrating micro bubbles and the vibration amplitudes of the bubbles for a given transmitted amplitude of the LF wave.

20. The instrument according to claim 12, where said processing means include means to estimate the phase of the $2^{nd}$ order transfer function between incident LF pressure oscillation and the amplitude bubble volume vibration from the timing $t_m$ that gives the maximal detection parameter $D_m$.

21. The instrument according to claim 20, where the processing means includes a) means for detection of the maximal detection parameter $D_m$ for at least two different frequencies of the LF beam, and b) means for estimating the following parameters of the $2^{nd}$ order approximation to the transfer function from incident pressure amplitude to bubble volume vibration i) the angular resonance frequency $\hat{\omega}_0$ for the bubble ii) the absorption coefficient $\hat{\zeta}$ of the $2^{nd}$ order approximation to the incident LF pressure to bubble volume transfer function, iii) the gain $\hat{K}_V$ of the $2^{nd}$ order approximation to the incident LF pressure to bubble volume transfer function.

22. The instrument according to claim 21, where the processing means comprises means to estimate at least one of the following vibration parameters for the tissue surrounding a bubble that is filling a part of a vessel i) the ratio of the tissue shear wave velocity $c_s$ to the vessel radius $a_V$ from estimates of the angular resonance frequency $\hat{\omega}_0$ of the bubble, and ii) the real part of tissue shear stiffness for a known radius of the vessel from estimates of the angular resonance frequency $\hat{\omega}_0$ of the bubble, and iii) the imaginary part of tissue shear stiffness for a known radius of the vessel from the estimate of the angular resonance frequency $\hat{\omega}_0$ of the bubble.

23. A method for estimating parameters related to the surface or volume displacement vibration amplitude of at least one micro-bubble brought to vibration by an ultrasound wave of amplitude $P_L$ and angular frequency $\omega_L$ transmitted along a LF beam with a given propagation direction along the unit vector $\underline{e}_L$, comprising a) transmitting towards said at least one micro-bubble at least two high frequency (HF) pulses with $\omega_H > 5\omega_L$ along one HF beam along the unit vector $\underline{e}_H$ at different times, b) directing at least one HF receive beam towards the region of the at least one micro-bubble with a direction $\underline{e}_{HR}$, the LF transmit and the HF transmit and receive beams are arranged so that they overlap at least in an observation region that includes said at least one micro-bubble, c) arranging the transmit timing of each of the transmitted HF pulses so that the pulses hits said at least one micro-bubble at different phases the LF oscillation, d) receiving at least two HF receive signals scattered from each said at least two transmitted HF pulses, and e) processing the at least two HF receive signals, to for each said at least one micro-bubble to produce an estimate of a bubble vibration parameter that gives one or both of the relative vibration of one or both of i) the bubble volume vibration relative to the resting bubble volume, and ii) a parameter related to relative bubble volume vibration wherein the HF transmit beam is directed in close to the same direction as the LF transmit beam and the LF transmit and HF transmit and HF receive beams are positioned so that the three beams overlap in a region around said at least one micro-bubble, to produce estimates of said bubble vibration parameter for each said at least one micro-bubble;

wherein a long LF pulse of duration $T_L$ is transmitted towards said at least one micro-bubble, where $T_L$ is longer than $T_R$, preferably longer than N*TR, where $T_R$ is the propagation time from HF transmit transducer to said at least one micro-bubble, and a set $S_N$ of N≥1 groups $G_n$, comprising two HF pulses are transmitted at a reference time $t_n$ for each group, and internal timing within each group is selected so that at least two pulse complexes hits the bubble at opposite polarities of the LF oscillation, and the processing includes combining the scattered HF pulses from said at least two HF pulses for each group $G_n$ to produce a detection parameter $D_n$ for group $G_n$ and each said at least one micro-bubble, and for each said at least one micro-bubble, the detection parameter Dm for the group $G_m$, that gives maximal detection parameter for all $G_n \cdot S_N$ is used as an estimate to obtain an estimate of the amplitude of said bubble vibration parameter.

24. The method according to claim 23, where the HF receive signals are compensated by one or both of i) a nonlinear propagation delay, and ii) a nonlinear pulse form distortion in the processing chain to produce estimates of said bubble vibration parameter for each said at least one micro-bubble.

25. The method according to claim 23, where said parameter related to relative bubble volume vibration is the average surface normal vibration amplitude relative to a radius of the bubble.

26. The method according to claim 25, where the value of the average surface normal is used to set the transmit amplitude of the LF wave.

27. The method according to claim 23, where the LF beam is focused onto in the therapeutic region.

28. The method according to claim 23, where the HF beam is broad with width less than the LF beam in the observation region, and several multi-focused parallel HF receive beams are generated to provide spatial resolution in the estimates of said bubble vibration parameter for a group of micro-bubbles.

29. The method according to claim 23, where scanning in 2 or 3 dimensions of one or more of
i) the HF receive beam direction, and
ii) the HF transmit beam direction, and
iii) the LF beam direction
to produce images of vibrating micro bubbles and the vibration amplitudes of the bubbles for a given transmitted amplitude of the LF wave.

30. An instrument for obtaining estimates of parameters related to the surface or volume displacement vibration amplitude of at least one micro-bubble brought to vibration by an ultrasound wave of amplitude PL and angular frequency $\omega_L$, comprising a) means for transmitting towards said at least one micro-bubble ai) at least one LF pulse along a LF transmit beam with a transmit beam direction along a unit vector $\underline{e}_L$, said LF pulse comprising a long LF pulse of duration $T_L$ towards said at least one micro-bubble, where $T_L$ is long, preferably longer than $NT_R$ where $T_R$ is the propagation time from HF transmit transducer to said at least one micro-bubble, and a set $S_N$ of N≥1 groups $G_n$ comprising two HF pulses transmitted at a reference time $t_n$ for each group, and selecting internal timing within each group so that at least two pulse complexes hits the bubble at opposite polarities of the LF oscillation and aii) at least two high frequency (HF) pulses with $\omega_H > 5 \omega_L$ along a HF beam along the unit vector $\underline{e}_H$ at different times, and aiii) means for arranging the transmit timing of each of the transmitted HF pulses so that the pulses hit said at least one micro-bubble at different phases the LF oscillation, wherein said means for transmitting include means for transmitting said HF transmit beam in close to the same direction as the LF transmit beam, and b) means for receiving that includes i) means for directing at least one HF receive beam with direction $\underline{e}_{HR}$ to produce an overlap region (OR) with the LF and HF transmit beams that includes the at least one micro-bubble, and ii) means for receiving at least two HF receive signals scattered from each said at least one micro-bubble from said at least two transmitted HF pulses, and wherein said means for receiving include means for directing the HF receive beam so that the LF transmit and HF transmit and HF receive beams overlap at the position of said at least one micro-bubble; and c) means for processing the at least two HF receive signals, to for each said at least one micro-bubble to produce an estimate of a bubble vibration parameter that gives one or both of the relative vibration of one or both of i) the bubble volume vibration relative to the resting bubble volume, and ii) a parameter related to relative bubble volume vibration, wherein said means for processing includes means for combining the received scattered HF pulses from said at least two HF transmit pulses for each group $Gh_n$ to produce a detection parameter $D_n$ for group $G_n$ and each said at least one micro-bubble, and means for selecting for each said at least one micro-bubble the detection parameter $D_m$ for group $G_m$, that gives maximal detection parameter for all $G_n \cdot S_N$, Said $G_m$ is used to obtain an estimate of the amplitude of said bubble vibration parameter for each said at least one micro-bubble.

31. The instrument according to claim 30, where said processing means include means for compensating the HF receive signals by one or both of i) a nonlinear propagation delay, and ii) a nonlinear pulse form distortion in the processing chain to produce estimates of said bubble vibration parameter for each said at least one micro-bubble.

32. The instrument according to claim 15, where the LF beam is focused onto in the therapeutic region.

33. The instrument according to claim 16, where the HF transmit beam is broad with width less than the LF beam in the observation region, and several multi-focused parallel HF receive beams are generated to provide spatial resolution in the estimates of said bubble vibration parameter for a group of micro-bubbles.

34. The instrument according to claim 17, where said parameter related to relative bubble volume vibration is the average surface normal vibration amplitude relative to a radius of the bubble.

35. The instrument according to claim 34, comprising means to use the value of the average surface normal to set the transmit amplitude of the LF wave.

36. The instrument according to claim 30, where said transmit and receive means comprises means for scanning in 2 or 3 dimensions of one or more of
   i) the HF receive beam direction, and
   ii) the HF transmit beam direction, and
   iii) the LF beam direction
   to produce images of vibrating micro bubbles and the vibration amplitudes of the bubbles for a given transmitted amplitude of the LF wave.

* * * * *